(12) United States Patent
Bingol et al.

(10) Patent No.: US 10,729,806 B2
(45) Date of Patent: Aug. 4, 2020

(54) ADHESIVE COMPOSITION

(71) Applicant: Coloplast A/S, Humlebaek (DK)

(72) Inventors: Bahar Bingol, Copenhagen OE (DK); Kristoffer Hansen, Naerum (DK)

(73) Assignee: Coloplast A/S, Humlebaek (DK)

( * ) Notice: Subject to any disclaimer, the term of this patent is extended or adjusted under 35 U.S.C. 154(b) by 242 days.

(21) Appl. No.: 15/569,777

(22) PCT Filed: Apr. 28, 2016

(86) PCT No.: PCT/DK2016/050109
§ 371 (c)(1),
(2) Date: Oct. 27, 2017

(87) PCT Pub. No.: WO2016/173600
PCT Pub. Date: Nov. 3, 2016

(65) Prior Publication Data
US 2018/0133360 A1 May 17, 2018

(30) Foreign Application Priority Data

Apr. 30, 2015 (DK) ................................. 2015 70255
Oct. 8, 2015 (WO) ................ PCT/DK2015/050305
Apr. 13, 2016 (DK) ................................. 2016 70225

(51) Int. Cl.
*C09J 183/04* (2006.01)
*A61L 24/04* (2006.01)
*A61L 24/00* (2006.01)
*A61M 27/00* (2006.01)
*A61F 5/443* (2006.01)
*A61M 25/00* (2006.01)
*C08G 77/18* (2006.01)
*C08G 77/16* (2006.01)

(52) U.S. Cl.
CPC ............ *A61L 24/043* (2013.01); *A61F 5/443* (2013.01); *A61L 24/001* (2013.01); *A61L 24/0021* (2013.01); *A61L 24/0031* (2013.01); *A61L 24/0089* (2013.01); *A61M 27/00* (2013.01); *C09J 183/04* (2013.01); *A61L 2400/14* (2013.01); *A61M 25/0017* (2013.01); *C08G 77/16* (2013.01); *C08G 77/18* (2013.01)

(58) Field of Classification Search
None
See application file for complete search history.

(56) References Cited

U.S. PATENT DOCUMENTS

| | | | | |
|---|---|---|---|---|
| 3,373,745 A * | 3/1968 | Benfield | .................. | A61F 5/443 264/222 |
| 4,143,088 A * | 3/1979 | Favre | ....................... | C08K 5/54 525/477 |
| 4,192,785 A * | 3/1980 | Chen | ....................... | A61F 5/443 523/118 |
| 4,204,540 A * | 5/1980 | Cilento | .................... | A61F 5/443 604/336 |
| 4,623,593 A * | 11/1986 | Baier | ...................... | A61L 27/18 264/338 |
| 4,831,070 A * | 5/1989 | McInally | ................. | A61L 15/58 524/267 |
| 5,009,648 A * | 4/1991 | Aronoff | .................. | A61F 5/445 604/332 |
| 5,051,455 A * | 9/1991 | Chu | ......................... | C08K 9/04 523/212 |
| 5,384,174 A * | 1/1995 | Ward | ...................... | A61F 5/443 206/440 |
| 5,473,026 A * | 12/1995 | Strong | ................... | C09J 183/04 525/477 |
| 5,504,174 A * | 4/1996 | Onishi | .................... | C08L 83/04 525/478 |
| 5,580,915 A * | 12/1996 | Lin | ........................ | C09J 183/02 524/267 |
| 5,698,653 A * | 12/1997 | Lucas | .................... | C08K 5/098 524/731 |
| 5,782,916 A | 7/1998 | Pintauro et al. | | |
| 6,068,852 A | 5/2000 | Shah | | |
| 6,072,012 A * | 6/2000 | Juen | ....................... | C08G 77/44 525/474 |
| 6,095,996 A | 8/2000 | Steer et al. | | |
| 6,437,039 B1 * | 8/2002 | Ahmed | ................ | C09D 183/04 524/261 |
| 6,520,943 B1 * | 2/2003 | Wagner | ................... | A61F 5/443 604/332 |
| 6,890,601 B2 * | 5/2005 | Griswold | ............... | C09J 183/04 427/387 |
| 7,651,485 B2 * | 1/2010 | Fattman | .................. | A61F 5/443 428/391 |

(Continued)

FOREIGN PATENT DOCUMENTS

| | | |
|---|---|---|
| EP | 0315333 A2 | 5/1989 |
| EP | 2371920 A1 | 10/2011 |
| EP | 2524954 A1 | 11/2012 |
| RU | 2434906 C2 | 11/2011 |
| RU | 2481363 C2 | 5/2013 |
| WO | 9855057 A1 | 12/1998 |
| WO | 2006002425 | 1/2006 |

(Continued)

*Primary Examiner* — Robert S Loewe

(74) *Attorney, Agent, or Firm* — Coloplast Corp., Coloplast A/S; Nick Baumann

(57) ABSTRACT

Moisture-curable adhesive compositions, their preparation and use are disclosed herein. The moisture-curable adhesive compositions include one or more reactive polymers, such as reactive silicone polymers, one or more adhesive components, such as a silicone pressure sensitive polymer(s) (PSAs), a cross-linker and a catalyst. Typically, the reactive silicone polymer or polymers are hydroxyl terminated polydimethylsiloxanes (PDMS) having at least two hydroxyl functionalities associated with the polymer(s).

19 Claims, No Drawings

(56) References Cited

U.S. PATENT DOCUMENTS

| | | | | |
|---|---|---|---|---|
| 8,298,367 B2* | 10/2012 | Beger | ................. | C08L 83/04 |
| | | | | 156/325 |
| 8,563,667 B2* | 10/2013 | Katayama | .............. | C09J 183/04 |
| | | | | 525/477 |
| 2004/0234786 A1* | 11/2004 | Giraud | ................. | B32B 3/10 |
| | | | | 428/447 |
| 2005/0107499 A1 | 5/2005 | Georgeau et al. | | |
| 2007/0191541 A1* | 8/2007 | Guennouni | .......... | C08K 5/0025 |
| | | | | 524/731 |
| 2008/0284106 A1 | 11/2008 | Maton et al. | | |
| 2009/0214458 A1* | 8/2009 | Brun | ................. | A61K 8/891 |
| | | | | 424/70.6 |

FOREIGN PATENT DOCUMENTS

| | | |
|---|---|---|
| WO | 2008118461 | 10/2008 |
| WO | 2010117744 A2 | 10/2010 |
| WO | 15082877 A1 | 6/2015 |

\* cited by examiner

ADHESIVE COMPOSITION

SUMMARY OF THE INVENTION

The present embodiments pertain to moisture-curable adhesive compositions, their use, and methods to prepare the compositions. These moisture-curable adhesive compositions include one or more reactive polymers, such as reactive silicone polymers, one or more adhesive components, such as a silicone pressure sensitive polymer(s) (PSAs), a cross-linker, and a catalyst. Typically, the reactive silicone polymer or polymers are hydroxyl terminated polydimethylsiloxanes (PDMS) having at least two hydroxyl functionalities associated with the polymer(s). Optional additives include, for example, silicone oil(s), absorbent material(s), fillers, etc.

DETAILED DESCRIPTION

One of the main concerns of people using ostomy appliances is that the ostomy adhesive attachment may be compromised resulting in leakage or even complete detachment of the ostomy appliance. Leakage is problematic not only in that it negatively affects the life quality of the ostomy device user but also because it will lead to skin problems. It is difficult to properly attach an adhesive to damaged skin, thus increasing the risk of further leakage and additional skin damage. There exists a need to further reduce the risk of leakage of ostomy devices.

A central challenge in the design of ostomy devices is that the device has to be attached to the skin of the ostomy device user. The skin is not an easy substrate for adhesion: It has a very large and highly irregular surface, it is often moist, and it stretches, bends, and moves as the ostomy user moves about. Also, many ostomy users have scar tissue in the area around the stoma.

Viewed in isolation, adhesion to the skin may be achieved in a number of ways. However, in the design of an adhesive suitable for use in an ostomy device, several other requirements should be considered. The ostomy adhesive should preferably be able to cope with the moisture evaporating from the skin underneath the ostomy adhesive. The ostomy adhesive should be able to stick to a moist surface, such as moist or sweaty skin, and should, after attachment, be able to somehow reduce accumulation of moisture at the skin surface. Accumulation of moisture at the skin surface can cause maceration of the skin, which is painful and which makes proper adhesion even more difficult to achieve. At the same time, it is of course preferable that the moisture and/or output from inside the collecting bag does not damage the adhesive or leak out to the surface of the ostomy user's skin.

In addition to adhering to the skin and handling moisture, an ostomy adhesive should also be able to remain attached to the skin while carrying a load, namely the collecting bag and its contents. Finally, ostomy adhesives should be able to be removed from the skin, while causing as little damage to the skin as possible and without disintegrating and/or leaving residue on the skin.

The present inventors have provided an adhesive composition, which is capable of preventing leakage by means of a combination of having a low viscosity in a first liquid state and being switchable to a second adhesive state with a sufficient peel force. The low viscosity ensures fast and good adhesion to the skin of a user and the sufficient peel force ensures that the adhesive remains securely attached and acts as a regular pressure sensitive adhesive during use. These effects combined lead to a lower risk of leakage from, e.g., an ostomy device attached with the instant adhesive composition.

In embodiments, the adhesive composition is adapted to prevent damage to the skin upon removal of the adhesive after use and/or upon repositioning of the adhesive during use. Damage to the skin may be in the form of stripping of the skin, meaning that skin cells are detached from the skin and removed together with the adhesive. Although some skin cells will usually detach from the skin and be removed together with the adhesive, excessive stripping of cells will lead to damage of the skin. Especially, if the skin is stripped of cells every time the adhesive is removed, this will result in painful damage to the skin and may compromise future adhesion to the damaged skin.

In embodiments, potential skin stripping is measured by attaching the adhesive composition to a paper substrate, such as a sheet of newspaper paper, and measuring the amount of paper fibre removed from the paper when the adhesive is removed. Removal of fibres from the paper will be an indication of the potential of the adhesive to cause stripping of the skin.

One way of looking at adhesion and risk of leakage is to consider leakage to be a result of a malfunctioning adhesive and/or an adhesive that has not been applied properly by the user. The present inventors have addressed both of these concerns. By providing an adhesive with a low viscosity, the adhesive will be easier to apply correctly in that it requires less manipulation by the user in order to properly flow into the skin surface. And by the combination of an adhesive that has flowed properly into the structure of the skin and at the same time has a sufficiently high peel force, it is ensured that the adhesive will also function properly once applied.

In order to determine peel force in a more detailed fashion, the present inventors measure both the normal, herein so-called "first", peel force. For this measurement, the adhesive is adhered to a substrate and then the force required to peel the adhesive off the substrate is measured as described in detail herein. Also, a second or "repeated" peel force is measured. This measurement is performed by first applying the adhesive to the substrate, peeling it off, as for the measurement of the first peel force, re-applying it to the substrate, and then measuring the force required to peel it a second time.

In the present context, the composition in the second adhesive state should behave like a pressure sensitive adhesive. This means that the composition should adhere to the substrate not only by means of mechanical interlocking, but also by proper non-mechanical adhesion.

If the adhesive composition is attached merely by mechanical interlocking between the substrate and the adhesive, it may initially remain well attached to the substrate. But if the mechanical bond between substrate and composition is broken, the composition will not easily be able to re-attach to the substrate. In other words, the first peel force of a mechanically attached composition may be sufficiently high, but the second peel force will certainly be very low and insufficient to secure maintained attachment to the substrate. Oftentimes, a purely mechanically attached composition cannot be re-applied to the substrate at all, following first peel.

Thus, it may not be easy to distinguish mechanical interlocking from proper adhesion by looking solely at the first peel force. However, the second peel force will clearly distinguish the two. In this way, the second peel force is one measure of the pressure sensitive adhesive characteristics of the adhesive composition. A sufficiently high second peel force will ensure that the composition acts in the cured adhesive state as a pressure sensitive adhesive in that it can be peeled off, re-applied, and still remain securely adhered.

When used on skin, it can be advantageous that the adhesive bond to the skin is somewhat dynamic and that detachment and re-adherence is possible on both a small and a large scale. Body movements may cause detachment of the adhesive from small areas of the skin and in some cases, the user may want to detach, adjust, and re-adhere the adhesive. This applies particularly to adhesives used for ostomy and wound care applications. Thus, it is advantageous that such adhesives have the characteristics of a pressure sensitive adhesive in the second adhesive state, at least in that they can be detached and re-attached to the substrate. In the present context, a pressure sensitive adhesive will exhibit a second repeated peel value, as measured herein, of at least 1 N/25 mm.

Adjusting the second peel force of a composition can be done, for instance, by adjusting the degree of crosslinking of the polymer used in the composition. The second peel force can also be affected by adding tackifiers and/or plasticizers to the composition. Increasing the content of tackifiers and plasticizers will lead to an increased second repeated peel force. Correspondingly, a lower content of tackifiers and/or plasticizers will lead to a lower second repeated peel force. Depending on the exact choice of tackifiers and plasticizers, the repeated peel force can be adjusted without at the same time significantly affecting the viscosity of the composition. Polymers, which are more or less miscible with the base polymer of the composition, may also be added to control repeated peel. Hydrocolloids, oils, and various fillers can also be used to adjust the second peel force. Generally, hydrocolloids and fillers will tend to reduce the peel force of the composition. The second peel force is measured as described herein.

As will be appreciated from the above, the desired characteristics of an ostomy adhesive are many and sometimes contradictory. It should be able to handle moisture from the skin, but at the same time should be able to contain or resist any moisture from inside the collecting bag. This may be achieved by striking a good balance between absorption, permeability, and erosion resistance. The ostomy adhesive should be able to adhere properly and stay securely attached to the skin, but it should also be easy to remove without causing damage to the skin. This may be achieved by making sure the first and/or second repeated peel force of the adhesive is sufficiently high to stay attached without being so high as to cause pain upon removal. The repeated peel force after switch should preferably be at least 1 N/25 mm, measured as described herein. In embodiments, the first and/or second repeated peel force is below 10 N/25 mm, such as below 5 N/25 mm. A peel force below, e.g., 10 N/25 mm will help to ensure ease of removal of the adhesive composition and will also help prevent tearing of skin adjacent to the attachment site of the adhesive composition. Pain during removal may also be reduced by keeping the peel force low. A first and/or second repeated peel force below 5 N/25 mm may contribute further to these effects. Also, the low viscosity in the first liquid state will ensure that the composition flows well into the structure of the skin and quickly attains good adhesion.

The adhesive used for ostomy appliances are typically pressure sensitive adhesives, meaning that application of pressure to the adhesive enhances the adhesive bond to the substrate, e.g., the skin. In several cases, ostomy bag users do not apply pressure enough to the adhesive base plate of the bag sufficiently to maintain the adhesive capabilities. By applying pressure to the pressure sensitive adhesive it is possible for the adhesive to faster wet and flow into the skin surface, hereby obtaining a large contact area and increasing the adhesive power. Current adhesive systems for attachment of ostomy device to the skin often require a high or prolonged pressure from the user in order to sufficiently flow into and wet the surface of the substrate.

Studies conducted by the inventors found that the time spent by ostomy users in applying the adhesive wafer to the skin varies a lot. In particular, 14 users were asked to apply an adhesive ostomy device to their own skin. The mean time used was around 30 seconds. The time spent in the experiment was as follows.

| % of users | Maximum time used (seconds) |
| --- | --- |
| 100.0% | 117 |
| 90.0% | 87 |
| 75.0% | 62 |
| 50.0% | 28 |
| 25.0% | 23 |
| 10.0% | 20 |
| 2.5% | 19 |

Instead of addressing the above problem by making the user apply more pressure—or pressure over an extended period of time—to the adhesive, the present inventors have found that it would be beneficial to construct an adhesive that takes into account the already existing application routine of users. In other words, the present inventors have aimed at constructing an adhesive composition that will work well with the current application routines of users rather than trying to change the habits of the ostomy users. The present inventors have found that there is a need to facilitate application of an ostomy device to the skin of the ostomy device user. Application should preferably be quick and straightforward, it should require as little strength and dexterity as possible, and it should result in a quickly established sufficient adhesion of the device to the skin of the user. The application should be straightforward and quick, even for elderly or disabled users.

In conclusion, the inventors have found that one challenge with typical pressure sensitive adhesives is that it takes a long time to achieve good adhesion to the skin. If a user cannot or does not allow the adhesive sufficient time to properly attach and for instance starts moving about before a good adhesion has been established, then this will increase the risk of the adhesive fully or partly detaching from the skin and, in the case of an ostomy device, leakage.

The above issues have been addressed by the inventors by providing a moisture-curable adhesive composition that can be applied to the skin with a low pre-cure viscosity and subsequently "switched" or "cured" by contact with moisture to a post-cure (or "wear") state with a higher viscosity and a sufficiently high peel force to allow it to remain securely attached to the skin of the user. Thus, embodiments provide a moisture curable adhesive composition as described herein. In the present context, "moisture curable" means that the composition can be "cured" or "switched" from a first or "application" state to a second or "wear" state by exposure to moisture.

Generally, curing of a moisture-curable material will lead to an increase in the cohesion of the material. The uncured material will generally have a low cohesion, which may be seen, e.g., by the material failing cohesively in a peel test. As the material is cured, the cohesion will rise and the material becomes less prone to falling apart and cohesive failure.

Moisture curing materials have been used to glue parts of medical devices before their use on or in the human body. In such materials, curing of the materials takes place before use.

Recently, TRIO SILKEN STOMA GEL™, a moisture curing based material to be used as accessory in ostomy care, emerged. This is an example of 1-part moisture curing material to be cured on skin. TRIO SILKEN STOMA GEL™ has a lower viscosity during the application compared to most accessories in the ostomy market. However, TRIO SILKEN STOMA GEL™ is not sticky during application and use, which prevents this material from being a good interface between a medical device, such as an ostomy device or a wound care product, and skin.

Adhesion of materials on skin is an important parameter when it comes to success of ostomy care accessories as well as devices. Detailed herein is provided a novel strategy for how to make one-part moisture curing materials, which are adherent to skin. The strategy involves mixing of sealants, either commercial sealants such as TRIO SILKEN STOMA GEL™ or a similar material, with sticky polymers based on silicone, such as BioPSAs. With the formulations reported herein, the stickiness of materials can be tuned by the type of sticky polymer used as well as by the properties of the sealant.

Start viscosity of moisture curing materials is an important parameter to consider when developing ostomy care accessories. Accessories can be in the form of a stoma gel as well as in the form of a ring. The rings generally have higher viscosity compared to the gels. Generally, moisture-curing materials should have a start viscosity, which is low enough for good wetting of skin but at the same time high enough to prevent shearing before the material is cured. Therefore, moisture-curing formulations with different start viscosities are provided. The viscosity of the sticky polymer, concentration of sealant, and concentration of fillers in the sealant are among the parameters used to customize the start viscosity of moisture curing materials.

The viscosity of a mass or composition is a measure of its resistance to gradual deformation by shear stress or tensile stress. For liquids, it corresponds to the informal notion of "thickness". For example, honey has a higher viscosity than water. In the context of the present invention, viscosity is measured as described in detail herein. In particular, the indicated viscosity is the absolute value of the complex viscosity, i.e., $|\eta^*|$, measured at a frequency of 0.01 Hz.

In embodiments, the composition before curing has a complex viscosity $|\eta^*|$ below 0.3 MPa s, below 0.25 MPa s, below 0.2 MPa s, below 0.1 MPa s, below 50 kPa s, below 10 kPa s, below 5 kPa s, below 1 kPa s, below 500 Pa s, below 100 Pa s, below 50 Pa s, below 10 Pa s, below 1 Pa s, in the range 0.1-0.4 MPa s, in the range 10-100 kPa s, in the range 1-10 kPa s, in the range 100-1,000 Pa s, in the range 10-100 Pa s, or in the range 1-10 Pa s.

In embodiments, the composition before curing has a complex viscosity $|\eta^*|$ of at least 1, 10, 20, or 50 Pa s. Such a minimum viscosity will ensure that the composition remains viscous enough to be easily handled and that any particulate components of the compositions, such as hydrocolloids, can be evenly distributed and do not simply "sink" to the bottom of the composition. This will help ensure stability of the composition and make handling of the composition easier. In embodiments, the composition before curing has a complex viscosity $|\eta^*|$ of at least 100, 500, 1,000, 2,500, 5,000, or 10,000 Pa s.

In embodiments, the complex viscosity after curing is at least 2 times, such as at least 5 times, such as at least 10 times, such as at least 20 times, such as at least 50 times, such as at least 100 times, such as at least 1,000 times, such as at least 10,000 times higher than the complex viscosity before curing.

Cure time can be measured and defined in a number of ways. For the present composition, the inventors have found that the cure is best described by the time for which the product do not shear when subjected to the loads that are typically seen within an ostomy product. Ideally, this would be almost instantaneous, but for most practical purposes, 10 min is acceptable and 5 min is preferred. Another useful measure for cure time is the time that will allow the user to remove the product without the product failing cohesively. Ideally, this time is shortly after the composition has been applied. Two hours is very good while in practice eight hours is sufficient for most users. Since few users change more than twice a day, 12 hours is likely to be a realistic number. For extended-wear products, which are for use over several days, a cure time of 24 hours or even 48 hours could be preferable. This would allow the user sufficient time to handle the product without cure, while still being able to remove the product when needed.

The present embodiments pertain to moisture-curable adhesive compositions that include a reactive component, such as hydroxyl-terminated polydimethylsiloxanes (PDMS), an adhesive component, a cross-linker, and a catalyst. The reactive component includes a reactive silicone polymer or a mixture of reactive silicone polymers. The reactive component includes at least a hydroxyl group at two ends of the polymer. The adhesive component includes a pressure sensitive silicone adhesive (PSA), such as a Dow Corning® material including, for example, 7-4600.

The adhesive compositions described herein can form free flowing films that can be cured with moisture, for example, from the skin. Initially the adhesive composition is a free flowing low viscosity liquid or paste and can penetrate micro and macro structures of the skin and skin imperfections. Upon "curing" with moisture, the coating becomes tacky and is able to retain adhesive properties over time. Thus, the adhesive is a moisture curable adhesive composition.

In embodiments, the adhesive compositions include one or more silicone oils and one or more fillers.

The moisture-curable adhesive compositions can be prepared by a variety of methods as disclosed herein. For example, a reactive silicone polymer, such as hydroxy terminated PDMS, a filler, a PSA silicone polymer, a cross-linker and a catalyst are mixed for a sufficient period of time to provide a free flowing liquid. The resultant moisture-curable adhesive can be placed into a container, such as tube, bottle, etc. for later application.

The moisture-curable adhesive compositions described herein are useful for the attachment of a medical device to a surface, such as skin. The moisture-curable adhesives described herein, upon curing with moisture, provide an adhesive that is tacky, is releasable from the interface between the skin and the medical device and which acts as a PSA, wherein the adhesive qualities remain such that the device can be reattached to the skin surface multiple times without loss of adhesiveness.

Further, the moisture-curable adhesive compositions described herein can be part of a packaged product or a "kit". The packaged product or kit generally includes instructions on how to apply the moisture-curable adhesive to a surface, such as skin, and subsequently, after the adhesive has cured for a sufficient period of time, is then adhered to a device, such as an ostomy device, a urine collecting device, a faecal management device, dressings (would dressings), a skin protective bandage, and wound drainage bandages.

The reactive components present in the embodiments are generally silicone polymers that are hydroxyl terminated polyalkyl siloxanes, such as for example, hydroxy (hydroxyl) terminated polydimethylsiloxane (PDMS).

In one aspect, the reactive silicone polymer comprises a polysiloxane of the formula (I):

$$X-R_1R_2Si-(O-SiR_1R_2)_n-Y \quad (I)$$

wherein X and Y are OH;

wherein $R_1$ and $R_2$ independently are the same or different and selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group; and wherein n is a number from 1 to 10,000, more particularly from 1 to 5,000, even more particularly from 1 to 1,000, in particular from 1 to 750, more particularly from 1 to 500, or from 1 to 250, or from 1 to 100, 10 to 50 or 1 to 25 and all ranges therebetween, including from 2 to 9,999, from 3 to 4875, from 5 to 1,000, from 10 to 100, from 50 to 250, etc.

In another aspect, the reactive silicone polymer or mixture of reactive silicone polymers comprises a polysiloxane of the formula (II):

$$(R_3O)_m-Si(R_4)_{3-m}-(O-SiR_1R_2)_n-Si(R_4)_{3-k}-(OR_3)_k \quad (II)$$

wherein k and m independently are integers from 0 to 3, provided that k+m>0;

wherein $R_1$ and $R_2$ are each independently as defined above;

$R_4$ is selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group;

$R_3$ is $C_1$-$C_{10}$ alkyl; and n is as defined above.

In still another aspect, the reactive silicone polymer or mixture of reactive silicone polymers comprises a polysiloxane of the formula (III):

$$W-Z-W \quad (III)$$

wherein W is selected from the group consisting of —Si($R_1$)$_2$OH and —Si(R")$_2$-(D)$_d$-R'"—SiR"$_k$(OR$_5$)$_{3-k}$, wherein D is —R'"—(Si(R")$_2$—O)$_r$—Si(R")$_2$— and R" is selected from the group consisting of a $C_1$-$C_6$ alkyl, a vinyl group, a phenyl group, and a fluorinated $C_1$-$C_6$ alkyl, R'" is a divalent hydrocarbon group, r is an integer between 1 and 6, and d is 0 or an integer from 1 to 1000, e.g., 1 to 100, $R_5$ is a $C_1$-$C_6$ alkyl or alkoxy group, and k has is 0, 1 or 2; wherein Z is a linear organic or polysiloxane polymer backbone.

"d" can have a range of 1 to 100, or 2 to 100, or 3 to 100 or 5 to 100, or 5 to 90 or 10 to 100, or 20 to 100 or 20 to 80 or 30 to 75 or 15 to 50 or 20 to 50 and all ranges encompassing from 1 to 100 and subranges thereof.

Z is a polysiloxane of the formula (IV):

$$-[SiO_{(4-p)/2}(R_1)_p]_b- \quad (IV)$$

wherein b is an integer from 50-5,000, p is on average 1.9-2.0, and $R_1$ is as defined above.

"p" can have a range of 50 to 5000, or 200 to 1000, or 300 to 1000 or 500 to 1000, or 500 to 900 or 100 to 1000, or 200 to 1000 or 200 to 800 or 300 to 750 or 150 to 500 or 200 to 500 and all ranges encompassing from 50 to 5,000 and subranges thereof.

In still another aspect, the viscosity of the reactive silicone polymer or mixture of reactive silicone polymers is from 10 to 900,000 cSt at 25° C., using a Brookfield viscometer or a rheometer with an appropriate spindle.

Suitable hydroxy terminated PDMS materials include, for example, the hydroxyl terminated PDMS material contained in Trio Silken moisture sensitive silicone polymer, DMS-S31, DMS-535, DMS-S45 and DMS-S51 (Gelest, Inc.) having a weight average molecular weight ($M_w$) range of 25,000 g/mol to 125,000 g/mol, number average molecular weight ($M_e$) of 13,000 g/mol to 55,000 g/mol, a PDI of 2 to 2.4, a molecular weight of 26,000 to 139,000 and viscosities (cSt) of 1000 to 150,000. The molecular weight analysis was done by GPC in tetrahydrofuran and PDMS standards were used to determine the molecular weight.

Not to be limited by theory, it should be understood, with reference to a "reactive silicone polymer", the term "reactive" is intended to denote that the hydroxyl groups of the silicone interact, undergo a condensation reaction, release water upon reacting, release an alcohol, such as methanol, or otherwise adhere and/or physically associate themselves with the PSA in the presence of a catalyst and/or a cross-linking agent. That is, a reaction takes place that involves the hydroxyl groups of the reactive silicone polymer with one or more of the remaining components of the adhesive composition including but not limited to, the catalyst, the cross-linker, and the pressure sensitive silicone material.

The moisture-curable adhesive compositions described herein include a polycondensed organopolysiloxane resin, which is a reaction product or products of a silanol terminated organopolysiloxane and a silicate organopolysiloxane resin containing at least one $RSiO_{3/2}$ or $SiO_{4/2}$ siloxy unit in the presence of a base, such as ammonia. The polycondensed organopolysiloxane resin can also be called a pressure sensitive silicone adhesive and will be used interchangeably throughout.

As used herein, "silicone resin" refers to any organopolysiloxane containing at least one ($RSiO_{3/2}$), or ($SiO_{4/2}$) siloxy unit. As used herein in its broadest sense, a silicone PSA refers to the reaction products resulting from reacting a hydroxyl endblocked "linear" organopolysiloxane, as described above, with a "resin" organopolysiloxane, wherein the resin organopolysiloxane contains at least one ($RSiO_{3/2}$), or ($SiO_{4/2}$) siloxy unit.

Organopolysiloxanes are polymers containing siloxy units independently selected from ($R_3SiO_{1/2}$), ($R_2SiO_{2/2}$), ($RSiO_{3/2}$), or ($SiO_{4/2}$) siloxy units, where R may be any organic group. These siloxy units are commonly referred to as M, D, T, and Q units, respectively. These siloxy units can be combined in various manners to form cyclic, linear, or branched structures. The chemical and physical properties of the resulting polymeric structures vary depending on the number and type of siloxy units in the organopolysiloxane. "Linear" organopolysiloxanes typically contain mostly D or ($R_2SiO_{2/2}$) siloxy units, which results in polydiorganosiloxanes that are fluids of varying viscosity, depending on the "degree of polymerization" or DP as indicated by the number of D units in the polydiorganosiloxane. "Linear" organopolysiloxanes typically have glass transition temperatures ($T_g$) that are lower than 25° C. "Resin" organopolysiloxanes result when a majority of the siloxy units are selected from T or Q siloxy units. When T siloxy units are predominately used to prepare an organopolysiloxane, the resulting organosiloxane is often referred to as a "silsesquioxane resin". When M and Q siloxy units are predominately used to prepare an organopolysiloxane, the resulting organosiloxane is often referred to as a "MQ resin". Alternatively, the formula for an organopolysiloxane may be designated by the average of the siloxy units in the organopolysiloxane as follows; $R_nSiO_{(4-n)/2}$, where the R is independently any organic group, alternatively a hydrocarbon, or alternatively an alkyl group, or alternatively methyl. The value of n in the average formula may be used to characterize the organopolysiloxane. For example, an average value of n=1 would indicate a predominate concentration of the ($RSiO_{3/2}$) siloxy unit in the organopolysiloxane, while n=2 would indicate a predominance of ($R_2SiO_{2/2}$) siloxy units. As used herein, "organopolysiloxane resin" refers to those organopolysiloxanes having a value of n less than 1.8 in the average formula $R_nSiO_{(4-n)/2}$, indicating a resin.

The silicone resin may independently comprise (i) ($R^1_3SiO_{1/2})_a$, ($R^2_2SiO_{2/2})_b$, (iii) ($R^3SiO_{3/2})_c$, and (iv) ($SiO_{4/2})_d$ siloxy units, providing there is at least one T or Q siloxy unit in the silicone resin molecule. The amount of each unit present in the silicone resin is expressed as a mole fraction (i.e. a, b, c, or d) of the total number of moles of all M, D, T, and Q units present in the silicone resin. Any such formula used herein to represent the silicone resin does not indicate structural ordering of the various siloxy units. Rather, such formulae are meant to provide a convenient notation to describe the relative amounts of the siloxy units in the silicone resin, as per the mole fractions described above via the subscripts a, b, c, and d. The mole fractions of the various siloxy units in the present organosiloxane block copolymers, as well as the silanol content, may be readily determined by $^{29}Si$ NMR techniques.

The silicone resin may also contain silanol groups (SiOH). The amount of silanol groups present on the silicone resin may vary from 0.1 to 35 mole percent silanol groups [—SiOH], alternatively from 2 to 30 mole percent silanol groups [—SiOH], alternatively from 5 to 20 mole percent silanol groups [—SiOH]. The silanol groups may be present on any siloxy units within the silicone resin.

The molecular weight of the silicone resin is not limiting. The silicone resin may have a weight average molecular weight ($M_w$) of at least 1,000 g/mole, alternatively a weight average molecular weight of at least 2,000 g/mole, alternatively a weight average molecular weight of at least 5,000 g/mole, alternatively a weight average molecular weight of at least 10,000 g/mole. The weight average molecular weight may be readily determined using Gel Permeation Chromatography (GPC) techniques.

In one embodiment, the silicone resin is a MQ silicone. The silicone resin may be a MQ resin comprising at least 80 mole % of siloxy units selected from ($R^1_3SiO_{1/2})_a$ and ($SiO_{4/2})_d$ units (that is a+d≥0.8), where $R^1$ is an alkyl group having from 1 to 8 carbon atoms, an aryl group, or a carbinol group, with the proviso that at least 95 mole % of the $R^1$ groups are alkyl groups, a and d each have a value greater than zero, and the ratio of a/d is 0.5 to 1.5.

The $R^1$ units of the MQ resin are independently an alkyl group having from 1 to 8 carbon atoms, an aryl group, or a carbinol group. The alkyl groups are illustrated by methyl, ethyl, propyl, butyl, pentyl, hexyl, and octyl. The aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl.

MQ resins suitable for use herein and methods for their preparation, are known in the art. For example, U.S. Pat. No. 2,814,601 to Currie et al., Nov. 26, 1957, which is hereby incorporated by reference, discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is disclosed in U.S. Pat. No. 2,857,356 to Goodwin, Oct. 21, 1958, which is hereby incorporated by reference. Goodwin discloses a method for the preparation of an MQ resin by the cohydrolysis of a mixture of an alkyl silicate and a hydrolyzable trialkylsilane organopolysiloxane with water.

The MQ resins useful herein may contain D and T units. The MQ resins may also contain hydroxy groups. Typically, the MQ resins have a total weight % hydroxy content of 2-10 weight %, alternatively 2-5 weight %. The MQ resins can also be further "capped" wherein residual hydroxy groups are reacted with additional M groups.

In one embodiment, the silicone resin is a silsesquioxane resin. The silsesquioxane resin may be a silsesquioxane resin comprising at least 80 mole-% of $R^3SiO_{3/2}$ units, where $R^3$ in the above trisiloxy unit formula is independently a $C_1$ to $C_{20}$ hydrocarbyl, or a carbinol group. As used herein, hydrocarbyl also includes halogen-substituted hydrocarbyls. $R^3$ may be an aryl group, such as phenyl, naphthyl, anthryl group. Alternatively, $R^3$ may be an alkyl group, such as methyl, ethyl, propyl, or butyl. Alternatively, $R^3$ may be any combination of the aforementioned alkyl or aryl groups. Alternatively, $R^3$ is phenyl, propyl, or methyl. In one embodiment, at least 40 mole % of the $R^3$ groups are propyl, referred herein as T-propyl resins, since the majority of the siloxane units are T units of the general formula $R^3SiO_{3/2}$ where at least 40 mole %, alternatively 50 mole %, or alternatively 90 mole % of the $R^3$ groups are propyl. In another embodiment, at least 40 mole % of the $R^3$ groups are phenyl, referred herein as T-phenyl resins, since the majority of the siloxane units are T units of the general formula $R^3SiO_{3/2}$ where at least 40 mole %, alternatively 50 mole %, or alternatively 90 mole % of the $R^3$ groups are phenyl. In yet another embodiment, $R^3$ may be a mixture of propyl and phenyl. When $R^3$ is a mixture of propyl and phenyl, the amounts of each in the resin may vary, but typically, the $R^3$ groups in the silsesquioxane resin may contain 60-80 mole percent phenyl and 20-40 mole percent propyl.

A silsesquioxane can be represented by:

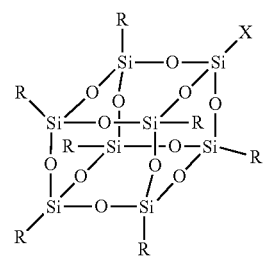

wherein R is a group as described above and X is a functional group, such as an OH or other reactive group as described herein. It should be understood from these discussions that one or more of the R groups may also be a functional group and therefore not limited to non-reactive groups, such as alkyl groups.

Silsesquioxane resins are known in the art and are typically prepared by hydrolyzing an organosilane having three hydrolyzable groups on the silicon atom, such as a halogen or alkoxy group. Thus, silsesquioxane resins can be obtained by hydrolyzing propyltrimethoxysilane, propyltriethoxysilane, propyltripropoxysilane, or by co-hydrolyzing the aforementioned propylalkoxysilanes with various alkoxysilanes. Examples of these alkoxysilanes include methyltrimethoxysilane, methyltriethoxysilane, methyltriisopropoxysilane, dimethyldimethoxysilane, and phenyltrimethoxysilane. Propyltrichlorosilane can also be hydrolyzed alone, or in the presence of alcohol. In this case, co-hydrolyzation can be carried out by adding methyltrichlorosilane, dimethyldichlorosilane, phenyltrichlorosilane, or similar chlorosilanes and methyltrimethoxysilane, methyltriethoxysilane, methyltriisopropoxysilane, or similar methylalkoxysilane. Alcohols suitable for these purposes include methanol, ethanol, n-propyl alcohol, isopropyl alcohol, butanol, methoxy ethanol, ethoxy ethanol, or similar alcohols. Examples of hydrocarbon-type solvents which can also be concurrently used include toluene, xylene, or similar aromatic hydrocarbons; hexane, heptane, isooctane, or similar linear or partially branched saturated hydrocarbons; and cyclohexane, or similar aliphatic hydrocarbons.

The silsesquioxane resins suitable in the present disclosure may contain M, D, and Q units, but typically, at least 80 mole-%, alternatively 90 mole-% of the total siloxane units are T units. The silsesquioxane resins may also contain hydroxy and/or alkoxy groups. Typically, the silsesquioxane resins have a total weight % hydroxy content of 2-10 weight % and a total weight % alkoxy content of up to 20 weight %, alternatively 6-8 weight % hydroxy content and up to 10 weight % alkoxy content.

As used herein, "silicone resin" also encompasses silicone-organic resins. Thus, silicone-organic resins includes silicone-organic copolymers, where the silicone portion contains at least one $(RSiO_{3/2})$, or $(SiO_{4/2})$ siloxy unit. The silicone portion of the silicone-organic resin may be any of the silisesquioxane or MQ resins as described above. The organic portion may be any organic polymer, such as those derived by free radical polymerization of one or more ethylenically unsaturated organic monomers. Various types of ethylenically unsaturated and/or vinyl containing organic monomers can be used to prepare the organic portion including; acrylates, methacrylates, substituted acrylates, substituted methacrylates, vinyl halides, fluorinated acrylates, and fluorinated methacrylates, for example. Some representative compositions include acrylate esters and methacrylate esters such as methyl acrylate, ethyl acrylate, butyl acrylate, 2-ethylhexyl acrylate, methyl methacrylate, decyl acrylate, lauryl acrylate, isodecyl methacrylate, lauryl methacrylate, and butyl methacrylate; substituted acrylates and methacrylates such as hydroxyethyl acrylate, perfluorooctyl acrylate, hydroxypropyl acrylate, hydroxypropyl methacrylate, and hydroxyethyl methacrylate; vinyl halides such as vinyl chloride, vinylidene chloride, and chloroprene; vinyl esters such as vinyl acetate and vinyl butyrate; vinyl pyrrolidone; conjugated dienes such as butadiene and isoprene; vinyl aromatic compounds such as styrene and divinyl benzene; vinyl monomers such as ethylene; acrylonitrile and methacrylonitrile; acrylamide, methacrylamide, and N-methylol acrylamide; and vinyl esters of monocarboxylic acids The silicone resin selected may also be a combination(s) of any of the aforementioned silicone resins.

The silicone PSA may be the reaction product of a hydroxy endblocked polydialkylsiloxane polymer, such as a polydimethylsiloxane polymer and a hydroxy functional silicate or silicone resin. Typically, the hydroxy functional silicate resin is a trimethylsiloxy and hydroxy endblocked silicate resin, such as the silicone resins described above. For example, the polydimethylsiloxane polymer and hydroxy functional silicate resin are reacted in a condensation reaction to form the silicone PSA.

PSAs are disclosed in U.S. Pat. Nos. 4,584,355; 4,585,836; 5,726,256; 5,861,472; 6,337,086, all of which are hereby incorporated by reference for the purpose of disclosing the chemical compositions of PSAs useful herein.

Representative, non-limiting examples of commercially available PSA's suitable for use herein include: DOW CORNING® 7-4400 Adhesive, DOW CORNING® 7-4500 Adhesive, DOW CORNING® 7-4600 Adhesive, DOW CORNING® 7-4560.

The cross-linkers useful herein contain at least two hydrolysable groups and are selected from a silicone, an organic polymer, a monosilane molecule, and a disilane molecule.

In one aspect, the cross-linking agent is a monosilane of the formula (V):

$$R^{IV}_{4-q}Si(OR_5)_q \qquad (V)$$

wherein $R^{IV}$ is an organic radical comprising linear alkyl, branched alkyl, allyl, phenyl, substituted phenyl, acethoxy, and oxime groups;

wherein $R_5$ includes a hydrogen atom, methyl, and ethyl groups; and wherein q is 0 or an integer from 1 to 4.

In another aspect, the cross-linking agent is a disilane of the formula (VI):

$$Si(OR_7)_t R^V Si(OR_7)_q \qquad (VI)$$

wherein t and q independently are integers from 1 to 3;
wherein $R^V$ is an organic or poly-siloxane-based moiety; and
wherein $R_7$ is a hydrogen atom, methyl or ethyl groups.

Representative examples of cross-linking agents include, but are not limited to, methyltri(methoxy)silane (MTM), vinyltrimethoxysilane, methyltriethoxysilane, vinyltriethoxysilane, isobutyltrimethoxysilane (iBTM), ethyltrimethoxysilane, vinyltriethoxysilane, phenyltrimethoxysilane, oximosilanes, acetoxy silanes, acetonoxime silanes, and enoxy silanes.

Suitable catalysts include a metal-containing catalyst comprising a metal selected from the group consisting of tin, lead, antimony, iron, cadmium, barium, manganese, zinc, chromium, cobalt, nickel, aluminium, gallium, germanium, titanium and zirconium.

Generally, the catalyst includes organic functionality about the metal, such as linear and branched $C_1$ to $C_{12}$ alkyl groups or linear or branched $C_1$ to $C_{12}$ alkoxy groups.

Suitable examples of catalysts include, for example, organic tin metal catalysts such as alkyltin ester compounds including dibutyltin dioctoate, dibutyltin diacetate, dibutyltin dimaleate, dibutyltin dilaurate, butyltin 2-ethylhexoate. 2-ethylhexoates of iron, cobalt, manganese, lead and zinc may alternatively be used but titanate and/or zirconate based catalysts are preferred. Such titanates may comprise a compound according to the general formula $Ti[OR]_4$ where each R may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of R include but are not restricted to methyl, ethyl, propyl, isopropyl, butyl, tertiary butyl and a branched secondary alkyl group such as 2,4-dimethyl-3-pentyl. Preferably, when each R is the same, R is an isopropyl, branched secondary alkyl group or a tertiary alkyl group, in particular, tertiary butyl. The titanate or zirconate may be also chelated. The chelation may be with any suitable chelating agent such as an alkyl acetylacetonate such as methyl or ethylacetylacetonate. Obviously, a mixture of two or more catalysts can be used. Large selection of catalysts are given in EP1 254 192 and U.S. Pat. No. 3,856,839 (assigned to GE). U.S. Pat. No. 3,856,839 by Smith and Hamilton (assigned to General Electric) provides an extensive list of examples of M[OR']×[Z]z, where M is Ti.

Suitable titanium catalysts include, for example, titanium 2-ethylhexoxide (AKT 867, Gelest, Inc.) or titanium diisopropoxide bis(ethylacetoacetate (AKT865, Gelest, Inc.).

Adhesion promoters are hydrolysable in the presence of moisture and participate in the curing reaction. The organic functionality is believed to interact chemically with the substrate, thus ensuring a strong adhesion, while alkoxy functionality is cured with the matrix.

Suitable adhesion promoters include, for example, 3-aminopropyltrimethoxysilane, 3-aminopropyltriethoxysilane, 3-glycidoxypropyltrimethoxysilane, 2-3(3,4-epoxycyclohexyl)ethyltrimethoxysilane and 3-mercaptopropyltrimethoxysilanemethacryloxypropyltrimethoxysilane.

Suitable poly(dialkyl)siloxane oils, such as poly(dimethyl siloxane) are useful in the adhesive compositions described herein. The viscosity, measured using a Brookfield viscometer or a rheometer with an appropriate spindle, can vary from 5 cSt to 2,000,000 cSt and all values therebetween and ranges therebetween.

Water absorbent materials useful herein are suitably a particulate, solid water absorbent hydrophilic agent, such as a water-soluble or a water swellable (non-water soluble) hydrocolloid. The water soluble or water swellable (non-water soluble) hydrocolloids may suitably be selected from natural or synthetic hydrocolloids, such as guar gum, locust bean gum, pectin, alginates, gelatine, xantan or gum karaya, cellulose derivatives (e.g. salts of carboxymethyl cellulose such as sodium carboxymethyl cellulose, methyl cellulose and hydroxypropyl cellulose), sodium starch glycolate, polyvinylalcohol, polyacrylic acid (e.g. in the form of super absorbent particles SAP), and polyethylene glycol. Suitable hydrocolloids are, e.g., AQ 1045 (a branched water dispersible polyester) from Eastman, Pectin LM 12CG Z or Pectin USP/100 from CP Kelco, Natrosol (hydroxyethyl cellulose, non-ionic, water soluble ethers of cellulose and ethylene oxide) produced by AQUALON, Blanose 9H4XF (carboxymethyl cellulose) available from Hercules, Akucell® AF 2881 (carboxymethyl cellulose) available from Akzo, AquaSorb® (cross-linked carboxymethyl cellulose) from Aqualon, Sorbalg pH 470 (Calcium alginate) from Danisco Ingredients, Denmark. The hydrocolloids may also be selected from microcolloids (e.g having a particle size less than 20 microns or preferably below 5 or 2 microns).

The absorption capacity of a composition can be measured as defined herein. The water absorption capacity can be measured in one or both of the first and second states of the composition. The water absorption may be the same or different between the first and second states of the composition. In some embodiments, the water absorption capacity is higher in the first state than in the second state. A good absorption capacity will make the composition capable of handling moisture on the skin and will thereby prevent accumulation of moisture between the skin and the adhesive and thus help prevent damage to the skin, such as maceration.

In embodiments, the composition has an absorption of at least 0.01 g/cm$^2$/2 h, such as an absorption of at least 0.02, 0.03, 0.04, or 0.05 g/cm$^2$/2 h.

Oils and silicone fluids, such as trimethylsiloxy terminated PDMS can act as plasticizers for the present embodiments presented herein.

The filler may comprise a non-reinforcing filler such as talc, calcium carbonate, wood powder, or precipitated or fumed silica. More specifically, examples of such fillers include: calcium carbonate (such as dry ground grades of calcium carbonate, wet ground grades of calcium carbonate, beneficiated grades of calcium carbonate, precipitated grades of calcium carbonate, surface treated grades of calcium carbonate); kaolin and other clay-based minerals; talc (such as dry ground talc, calcined talc); quartz and silica, including natural silicas (such as crystalline silica, fused silica, microcrystalline silica, microcrystalline novaculite, diatomaceous silica, perlite) or synthetic silicas (such as fumed silica, precipitated silicas); mica (including ground grades of mica, white grades of mica, surface-modified grades of mica, metal-coated mica grades); metal oxides and other compounds (such as titanium dioxide, alumina trihydrate, wollastonite, barium sulphate, antimony oxide, magnesium oxide, magnesium hydroxide, calcium sulphate, anhydrous calcium sulphate, dihydrate calcium sulphate, feldspar and nepheline syenite); microspheres, solid microspheres, hollow microspheres (such as coated hollow microsphere fillers, metalite aluminium microspheres, polymer-encapsulated gas microspheres); synthetic silicates (such as aluminium silicate, mullite, sillimanite, cyanite, andalusite, synthetic alkali metal aluminosilicates, calcium silicate, magnesium silicate, zirconium silicate).

Suitable fillers include, for example, calcium carbonate, magnesium oxide, fumed hydrophobic silica, or lignin. Suitable hydrophobic fumed silicas include, for example AEROSIL® R812 (BET surface area g/cm$^2$ 230-290), AEROSIL® R974 (BET surface area g/cm$^2$ 150-190) or AEROSIL® 200 (BET surface area g/cm$^2$ 200±25).

Suitable tackifiers include, for example, C5-based petroleum resins, C9-based petroleum resins, dicyclopentadiene-based petroleum resins, rosin-based petroleum resins, polyterpene resins, terpene phenol resins, dibutyl phthalate, and dioctyl phthalate.

As discussed above, the present embodiments pertain to moisture-curable adhesive compositions that include one or more reactive polymers, which can be one or more hydroxyl terminated polydimethylsiloxanes (PDMS) having at least two hydroxyl functionalities associated with the polymer(s), one or more adhesive components, a cross-linker and a catalyst. The one or more adhesive components include silicone polymers or a mixture of silicone polymers such as PSA's. Optional additives include, for example, silicone oil(s), absorbent material(s), fillers, etc.

Generally, the total weight percent of the one or more hydroxyl terminated PDMS is 3 weight percent to 50 weight percent, in particular 3 weight percent to 42 weight percent, more particularly 4 weight percent to 40 weight percent and, in particular, 5 weight percent to 35 weight percent of the total weight of the adhesive composition equalling 100 weight percent. Additional ranges include 5 weight percent to 30 weight percent, in particular 10 weight percent to 25 weight percent, more particularly 15 weight percent to 25 weight percent and, in particular, 12 weight percent to 27 weight percent of the total weight of the adhesive composition equalling 100 weight percent. It should be understood that all ranges and values between 3 weight percent and 50 weight percent are included.

The total weight percent of the reactive silicone polymer is 5 weight percent to 50 weight percent, in particular 10 weight percent to 40 weight percent, more particularly 20 weight percent to 30 weight percent and, in particular, 15 weight percent to 35 weight percent of the total weight of the adhesive composition equalling 100 weight percent. It should be understood that all ranges and values between 5 weight percent and 50 weight percent are included.

The total weight of the cross-linker present is 0.2 weight percent to 5 weight percent, in particular 0.5 weight percent to 5 weight percent, more particularly 0.7 weight percent to 4 weight percent and, in particular, 1 weight percent to 5 weight percent of the total weight of the adhesive composition equalling 100 weight percent. Additional ranges include 0.5 weight percent to 4 weight percent, in particular 1 weight percent to 4 weight percent, more particularly 2 weight percent to 4 weight percent and, in particular, 1 weight percent to 3 weight percent of the total weight of the adhesive composition equalling 100 weight percent. It should be understood that all ranges and values between 0.2 weight percent and 5 weight percent are included.

The total weight concentration of the catalyst is 0.05 weight percent to 0.6 weight percent, in particular 0.05 weight percent to 0.5 weight percent, more particularly, 0.1 weight percent to 0.4 weight percent, and in particular, 0.2 weight percent to 0.3 weight percent of the total weight of the adhesive composition equalling 100 weight percent. Additional ranges include 0.1 weight percent to 0.5 weight percent, in particular 0.2 weight percent to 0.5 weight percent, more particularly 0.2 weight percent to 0.4 weight percent and, in particular, 0.3 weight percent to 0.4 weight percent of the total weight of the adhesive composition equalling 100 weight percent. It should be understood that all ranges and values between 0.05 weight percent and 0.6 weight percent are included.

The optional additive(s) total weight percent is 0 weight percent to 50 weight percent, in particular 0.5 weight percent to 45 weight percent, more particularly 1 weight percent to 40 weight percent, and in particular, 2 weight percent to 35 weight percent based on 100 weight percent total of the adhesive composition. Additional ranges include 3 weight percent to 30 weight percent, in particular 4 weight percent to 20 weight percent, more particularly 5 weight percent to 25 weight percent and, in particular, 5 weight percent to 10 weight percent of the total weight of the adhesive composition equalling 100 weight percent. It should be understood that all ranges and values between 0 weight percent to 50 weight percent are included.

In certain embodiments, the ratio of cross-linker to hydroxyl terminated polydimethylsiloxane(s) is 0.01:1, more particularly, 0.07:1, even more particularly, 0.05:1 and most particularly 0.04:1. It should be understood that all ratios and ranges between 0.01:1 to 0.07:1 are included.

In other embodiments, the ratio of hydroxyl terminated polydimethylsiloxane(s) to silicone polymer (PSA) is 0.05:1, more particularly, 0.6:1, even more particularly, 0.1:1 and most particularly 0.3:1. It should be understood that all ratios and ranges between 0.05:1 to 0.6:1 are included.

In still other embodiments, the ratio of silicone polymer (PSA) to cross-linker is 3:1, more particularly, 500:1, even more particularly, 50:1 and most particularly 100:1. It should be understood that all ratios and ranges between 3:1 to 500:1 are included.

In yet other embodiments, the ratio of hydroxyl terminated polydimethylsiloxane(s) to catalyst is 95:1, more particularly, 90:1, even more particularly, 70:1 and most particularly 50:1. It should be understood that all ratios and ranges between 50:1 to 95:1 are included.

In still yet other embodiments, the ratio of silicone polymer (PSA) to catalyst is 3:1, more particularly, 610:1, even more particularly, 100:1 and most particularly 250:1. It should be understood that all ratios and ranges between 3:1 to 610:1 are included.

In still further embodiments, the ratio of cross-linker to catalyst is 0.5:1, more particularly, 0.7:1, even more particularly, 2.6:1 and most particularly 3:1. It should be understood that all ratios and ranges between 0.5:1 to 3:1 are included.

Embodiments provide a method to releasably and adhesively attach a medical device to a skin surface comprising the steps:
  providing a medical device comprising a moisture-curable adhesive composition as disclosed herein;
  applying the moisture-curable adhesive to the skin surface;
  exposing the moisture-curable adhesive to moisture, thereby switching the moisture-curable adhesive from a liquid state to an adhesive state.

The "liquid state" may also be referred to as the "application state", i.e., the state of the composition in which it is applied to the skin. The "adhesive state" may also be referred to as the "wear state", i.e., the state in which the adhesive is worn on the skin. In embodiments, the composition has in the liquid state a complex viscosity $|\eta^*|$ below 0.4 MPa s. In embodiments, the composition has in the adhesive state a higher complex viscosity $|\eta^*|$ than the complex viscosity $|\eta^*|$ of the liquid state. In embodiments, the composition has in the adhesive state a second repeated peel force above 1 N/25 mm.

A composition having after curing a repeated peel force above 1 N/25 mm is advantageous because the peel force is sufficiently high to ensure that the adhesive remains properly attached to the substrate.

The present inventors have found that a composition having before curing a complex viscosity $|\eta^*|$ below 0.4 MPa s is advantageous in that it is capable of quickly flowing into the structure of a substrate, such as skin, and therefore is able to quickly wet the substrate and form a good basis for sufficient adhesion. Wetting means that the composition comes into direct contact with the surface of the substrate, including, where relevant, flowing into the micro and macro structures of the substrate.

In particular, within the field of pressure sensitive adhesives to be used for ostomy devices, our experiments have shown that a complex viscosity of 0.4 MPa s is the upper threshold for when a composition will flow sufficiently fast into the roughness of the skin and hereby obtain a desired adhesive contact in order to be able to seal around the stoma of a user within the period of time actually used by the average ostomy device user to attach the device.

In embodiments, the composition after curing has a second repeated peel force above a value selected from 1.5, 2, 2.5, 3, 3.5, 4, 4.5, 5, 6, 7, 8, 9, and 10 N/25 mm.

For instance, the second repeated peel force of the composition after curing could be above 2.5 N/25 mm.

In embodiments, the composition after curing has a G' in the range $10^3$-$10^5$ Pa or $10^3$-$10^4$ Pa or $10^4$-$10^5$ Pa, when measured as described herein at 1 Hz.

In embodiments, the composition after curing has a G" in the range $10^3$-$10^5$ Pa or $10^3$-$10^4$ Pa, when measured as described herein at 1 Hz.

The method may be carried out by a person other than the user to which the adhesive is attached. For instance, the method may be carried out by a commercial service provider assisting the user for a fee. Such commercial service providers exist and provide fee-based services to, e.g., ostomy users or people with wounds. The service may include the service provider removing and applying ostomy bags for the ostomy user or removing and applying wound dressings for a person with wounds.

The method may also be carried out in order to obtain a sample of the output from the ostomy user or wound exudate from the person with wounds. For instance, a healthcare professional may require a stoma output or wound exudate sample in order to make medical decisions or generally assess the physical state of a user. In such cases, the healthcare professional may order the sampling to be done by a professional service provider to ensure that the sampling happens correctly. Again, a fee-based commercial service provider would carry out the method with the aim of providing a sample to the healthcare professional. Such paid services exist on commercial terms and operate on a continuous and independent basis with an aim of financial gain. They are not exclusively dependent for their operation on the instructions of the user in question. For instance, they may work directly under the instructions of a healthcare professional.

In embodiments, the medical device is an ostomy device comprising an adhesive wafer comprising a moisture-curable adhesive composition as disclosed herein.

In some embodiments, the composition is for securing a medical device, such as a wound dressing or an ostomy device, to the skin of a user.

An ostomy device can be suitable for use in connection with a colostomy, an ileostomy, or a urostomy. An ostomy device may be a closed appliance.

An ostomy device may be an open appliance. An open ostomy appliance is configured to be emptied while the appliance is attached to the skin of the user; typically through a drainage port in the bottom of the bag.

An ostomy device can be a one-piece appliance comprising a) a base plate (also referred to as a body-side member or face plate) attachable around the stomal opening; and comprising b) attached to the base plate a collection bag.

An ostomy device can be a two-piece appliance comprising a) a base plate (also referred to as a body-side member) attachable around the stomal opening; and comprising b) a separate collection bag attachable to the base plate. In this two-piece configuration, the collection bag can be replaced without replacing the base-plate attached to the skin around the stomal opening. The separate collection bag may be attached to the body side member in any convenient manner known per se, e.g., via a mechanical coupling, such as a coupling ring, or by an adhesive flange.

In embodiments, the composition is for securing the adhesive wafer of a two-piece ostomy device to the skin of a user. It may be advantageous to use the present composition in connection with a two-piece device, since the switching of the adhesive can be carried out without the presence of the collecting bag, which may be attached after the adhesive has been switched.

Further embodiments are included in the following paragraphs, numbered consecutively from 1 through 42 as follows:

1. A moisture-curable adhesive composition comprising: a reactive component, wherein the reactive component comprises a reactive silicone polymer or a mixture of reactive silicone polymers; an adhesive component, wherein the adhesive component comprises a pressure sensitive silicone adhesive or a mixture of pressure sensitive adhesives; a cross-linker; and a catalyst.

2. The adhesive composition of paragraph 1, wherein the reactive silicone polymer or mixture of reactive silicone polymers comprises a polysiloxane of the formula (I):

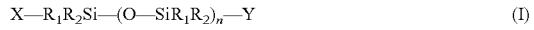

wherein X and Y are OH;

wherein $R_1$ and $R_2$ independently are the same or different and selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group; and wherein n is a number from 1 to 10,000.

3. The adhesive composition of paragraph 1, wherein the reactive silicone polymer or mixture of reactive silicone polymers comprises a polysiloxane of the formula (II):

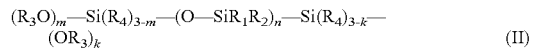

wherein k and m independently are integers from 0 to 3, provided that k+m>0;

wherein $R_1$, $R_2$, and $R_4$ independently are the same or different and selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group;

wherein $R_3$ is $C_1$-$C_{10}$ alkyl; and wherein n is a number from 1 to 10,000.

4. The adhesive composition of paragraph 1, wherein the reactive silicone polymer or mixture of reactive silicone polymers comprises a polysiloxane of the formula (III):

wherein W is selected from the group consisting of —Si(R1)2OH and —Si(R")2-(D)d-R'"—SiR"k(OR5)3-k, wherein D is —R'"—(Si(R")2-O)r-Si(R")2- and R" is selected from the group consisting of a $C_1$-$C_6$ alkyl, a vinyl group, a phenyl group, and a fluorinated $C_1$-$C_6$ alkyl, R'" is a divalent hydrocarbon group, r is an integer between 1 and 6, and d is 0 or an integer from 1 to 100, R5 is a $C_1$-$C_6$ alkyl or alkoxy group, and k has is 0, 1 or 2;

wherein Z is a linear organic or polysiloxane polymer backbone.

5. The adhesive composition of paragraph 4, wherein Z is a polysiloxane of the formula (IV):

wherein b is an integer from 50-5,000, p is on average 1.9-2.0, and $R_1$ is selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group.

6. The adhesive composition of paragraph 3, wherein $R_1$, $R_2$, and $R_4$ are the same or different and selected form the group consisting of monovalent alkyl radical with from 1 to 4 carbon atoms.

7. The adhesive composition of paragraph 6, wherein $R_1$ and/or $R_2$ and/or $R_4$ are methyl groups.

8. The adhesive composition of any of paragraphs 1 through 7, wherein the viscosity of the reactive silicone polymer or mixture of reactive silicone polymers is from 5 to 500,000 cSt, at 25° C.

9. The adhesive composition of paragraph 8, wherein the viscosity of the reactive silicone polymer or mixture of reactive silicone polymers is from 1,000-100,000 cSt.

10. The adhesive composition of any of paragraphs 1 through 9, wherein the pressure sensitive silicone adhesive of the adhesive component is a polycondensed organopolysiloxane resin which is a reaction product or products of a silanol terminated organopolysiloxane and a silicate organopolysiloxane resin containing at least one $RSiO_{3/2}$ or $SiO_{4/2}$ siloxy unit in the presence of a base to provide the polycondensed organopolysiloxane resin.

11. The adhesive composition of paragraph 10, wherein the silicate resin is an MQ type silicate resin.

12. The adhesive composition of paragraph 11, wherein the MQ resin comprises a core of three dimensional Q units comprising $SiO_{4/2}$ surrounded by a shell of M units comprising $R_3SiO$ and, optionally, one or more R can be an OH or H in the resin.

13. The adhesive composition of paragraph 12, wherein at least one R is a methyl group.

14. The adhesive composition of any of paragraphs 10 through 13, wherein the silanol terminated organopolysiloxane comprises a structure:

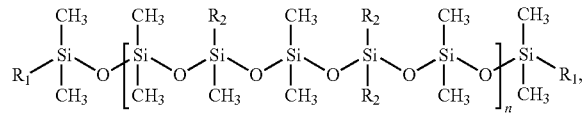

wherein $R_1$ is OH;
$R_2$ is methyl, phenyl, or vinyl; and
n is from 1 to 500, more particularly 10 to 400, even more particularly 50 to 300 and in particular 150 to 200 including all ranges and values therebetween.

15. The adhesive composition of paragraph 14, wherein $R_2$ is methyl.

16. The adhesive composition of paragraph 10, wherein the silicate organopolysiloxane resin comprises a silsesquioxane comprising a formula $[RSiO_{3/2}]_n$, wherein each R, individually, is H, an alkyl group, aryl group, a reactive functional group or an alkoxy group and n is 4 to 18.

17. The adhesive composition of paragraph 16, wherein one R is a reactive functional group when n equals 6, 8, 10, or 12.

18. The adhesive composition of paragraph 17, wherein the reactive functional group is a halodialkylsilylalkyl group, a dihaloalkylsilylalkyl group, a trihaloalkylsilyl group, a vinyl group, a silane group, a cyclicalklyhydroxide, an alkyl hydroxide, a cyclicalkyldihydroxide, an epoxide group, or an alkyl terminated epoxide group.

19. The adhesive composition of any of paragraphs 10 through 18, wherein the Mw of the silicate organopolysiloxane resin has a range of 1000 to 10,000 kDa.

20. The adhesive composition of any of paragraphs 1 through 19, wherein the pressure sensitive silicone adhesive of the adhesive component is selected from the group consisting of Dow Corning® 7-4400 Adhesive, Dow Corning® 7-4500 Adhesive, Dow Corning® 7-4600 Adhesive, Dow Corning® 7-4560.

21. The adhesive composition according to any of the preceding paragraphs, wherein the cross-linker contains at least two hydrolysable groups and is selected from the group consisting of a silicone, an organic polymer, a monosilane molecule, and a disilane molecule.

22. The adhesive composition according to any of the preceding paragraphs, wherein the cross-linker is a monosilane of the formula (V):

wherein $R^{IV}$ is an organic radical selected from the group consisting of linear alkyl, branched alkyl, allyl, phenyl, substituted phenyl, acethoxy, and oxime;
wherein $R_5$ is selected from the group consisting of hydrogen, methyl, and ethyl; and
wherein q is 0 or an integer from 1 to 4.

23. The adhesive composition according to any of the preceding paragraphs, wherein the cross-linker is a disilane of the formula (VI):

wherein t and q independently are integers from 1 to 3;
wherein $R^V$ is an organic or poly-siloxane-based moiety; and
wherein $R_7$ is selected from the group consisting of hydrogen, methyl, and ethyl.

24. The adhesive composition of paragraph 22, wherein the cross-linker is selected from the group consisting of methyltri(methoxy)silane (MTM), vinyltrimethoxysilane, methyltriethoxysilane, vinyltriethoxysilane, isobutyltrimethoxysilane (iBTM), ethyltrimethoxysilane, vinyltriethoxysilane, phenyltrimethoxysilane, oximosilanes, acetoxy silane, acetonoxime silane, and enoxy silane.

25. The adhesive composition according to any of the preceding paragraphs, wherein the catalyst is a metal-containing catalyst comprising a metal selected from the group consisting of tin, lead, antimony, iron, cadmium, barium, manganese, zinc, chromium, cobalt, nickel, aluminium, gallium, germanium, titanium and zirconium.

26. The adhesive composition of paragraph 25, wherein the catalyst is a titanium catalyst.

27. The adhesive composition according to any one of the preceding paragraphs, further comprising a hydrocolloid, wherein the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

28. The adhesive composition according to any one of the preceding paragraphs, further comprising a plasticizer.

29. The adhesive composition of paragraph 28, wherein the plasticizer is a polydimethylsiloxane oil.

30. The adhesive composition according to any one of the preceding paragraphs, wherein the adhesive composition comprises a filler.

31. The adhesive composition of paragraph 30, wherein the filler is calcium carbonate, magnesium oxide, hydrophobic fumed silica, or lignin.

32. The adhesive composition according to any one of the preceding paragraphs, further comprising tackifier.

33. The adhesive composition of paragraph 32, wherein the tackifier is a polyterpene resin.

34. The adhesive composition according to any one of the preceding paragraphs, further comprising an adhesion promoter.

35. The adhesive composition of paragraph 34, wherein the adhesion promoter is 3-aminopropyltrimethoxysilane, 3-aminopropyltriethoxysilane, 3-glycidoxypropyltrimethoxysilane, 2-3(3,4-epoxycyclohexyl)ethyltrimethoxysilane, 3-mercaptopropyltrimethoxysilane, or methacryloxypropyltrimethoxysilane.

36. The adhesive composition according to any one of the preceding paragraphs, wherein the adhesive composition is a one-part curable composition.

37. A method to prepare a moisture-curable adhesive composition according to any of paragraphs 1 through 26, comprising the step:
   combining one or more reactive silicone polymers, one or more pressure sensitive adhesives, a cross-linker and a catalyst to form the moisture-curable adhesive composition.

38. The method of paragraph 37, further comprising combining with the moisture-curable adhesive composition one or more of a hydrocolloid, a plasticizer, a filler or a tackifier.

39. A method to releasably and adhesively attach a medical device to a skin surface comprising the steps:
   providing a medical device comprising a moisture-curable adhesive composition according to any of paragraphs 1 through 36;
   applying the moisture-curable adhesive to the skin surface;
   exposing the moisture-curable adhesive to moisture, thereby switching the moisture-curable adhesive from an application state to a wear state.

40. A packaged product comprising:
   a moisture-curable adhesive composition according to any of paragraphs 1 through 36; and
   instructions to apply the moisture-curable composition to a skin surface.

41. The packaged product according to paragraph 40, wherein the packaged product further comprises a medical device associated with the packaged product.

42. The packaged product according to paragraph 41, wherein the medical device is an ostomy device.

Measurement Methods

Dynamic Mechanical Analysis (DMA) and Determination of G', G", Tan($\delta$), and Complex Viscosity $|\eta^*|$ The parameters G', G", tan($\delta$), and complex viscosity $|\eta^*|$ were measured as follows by a frequency sweep. The adhesives were pressed into a plate of 1 mm thickness. A round sample of 25 mm in diameter was cut out and placed in a Haake RheoStress 6000 rotational rheometer from Thermo Scientific. The geometry applied was parallel plates 25 mm and the shear stress was fixed at 5556 Pa and a gap size of 0.9-1.05 mm was applied to the sample in the beginning of the measurement to obtain a normal force of approximately 5 N. The measurements were carried out at 32° C.

For the complex viscosity $|\eta^*|$ the value measured at a frequency of 0.01 Hz was used. The test was run as a frequency sweep from 100 Hz to 0.01 Hz.

Peel Force

A sample of 25×100 mm was cut from the prepared sheet composition and a 25×300 mm piece of auxiliary tape was then added on the top of the sample. After 30 minutes of conditioning at 23° C. and 50% relative humidity, the sample was mounted in a tensile testing machine (INSTRON 5564 from Instron) and a 90-degree peel test was carried out from a Teflon substrate at a speed of 304 mm/min. The results are given in N/25 mm.

If required for the particular measurement, the samples were switched as described herein below for the individual compositions.

Samples were either attached to a substrate and peeled without having been switched at all ("non-switched"), attached to the substrate, then switched, and then peeled ("$1^{st}$ peel, switched on substrate"), attached to a substrate, then switched, then peeled, and then re-attached and peeled a second time ("$2^{nd}$ repeated peel, switched on substrate"), or first switched, then attached to the substrate, and then peeled ("peel when switched off substrate").

For the $2^{nd}$ repeated peel, switched on substrate, an additional 30 minutes of conditioning at 23° C. and 50% relative humidity was used before performing the second repeated peel.

The peel test was carried out in a climate-controlled room at 23° C. and 50% relative humidity. Peel angle was fixed at 90° and the peel speed was 304 mm/min. Dwell time, meaning the time the sample is rested before testing, was 30 minutes.

The Teflon substrate (2.0 mm PFTE, order no. SPTFE0020INA from RIAS, Roskilde, Denmark) mounted in steel plate was attached to the peel sledge. Adhesive strips were punched out from 0.4 mm thick adhesive sheets in the dimensions 25×100 mm. Auxiliary tape (25 mm width) was mounted on the adhesive with 10 mm overlap. The release liner was lifted in one end to make the overlap with the auxiliary tape. The adhesive was applied to the substrate by using an automatic roll with a load of 2 kg. The average of the mean load was reported as N/25 mm. The failure type, i.e. cohesive or adhesive failure, was observed, recorded, and reported with the peel data.

Moisture Absorption

Samples were prepared by thermoforming to a 0.5 mm thick adhesive film between two release liners. With a punching tool, samples were punched out. Sample size was 25×25 mm. The release liners were removed. The samples were glued to an object glass and placed in a beaker with physiological salt water and placed in an incubator at 37° C.

The sample was weighed at the outset (M(start)) and after 2 hours (M(2 hours). Before weighing, the object glass was dried off with a cloth. For a 25×25 mm sample, the area was 6.25 cm$^2$ (the surface edges were left out of the area). The moisture absorption may be calculated as: Water absorption after 2 hours=(M(2 hours)−M(start))/6.25 cm$^2$. The result is in the unit g/cm$^2$ per 2 hours.

Erosion Resistance

Erosion resistance is a measurement of how well the adhesive composition is able to resist breakdown when being exposed to moisture. Adhesive compositions capable of handling moisture are typically absorbent to some degree. The absorption will ensure that moisture on, e.g., the skin of a user is absorbed into the adhesive and thereby away from the skin surface where it might cause damage. Too much absorption, however, may destabilize the adhesive in that excessive swelling of the adhesive leads to decreased cohesion. As such, it is preferable to balance the absorption and cohesion of the adhesive composition. An adhesive with a well-balanced relationship between absorption and cohesion will typically exhibit a good resistance to erosion. A disk of the composition having a thickness of 0.5 mm, an outer diameter of 55 mm, and a hole with a diameter of 25 mm was coated on the top surface with an impermeable low-density polyethylene (LDPE) film.

The other side of the composition was attached to the surface of a dish by means of a double-sided adhesive tape and the system was mounted in a 1 l jar in an upright position in the middle of the jar. The jar was half filled with 0.9 wt-% NaCl in demineralised water and closed with a lid. The jar was placed in a lying position between two rollers and was rolled with a speed of 20 rpm in one direction and 20 rpm in the other direction for each 1 minute. If erosion was seen as a result of missing material this was noted. Also, the swelling (in one side) in mm was measured and the result reported as the average of two independent measurements. This result of this erosion measurement is an indication of the resistance to water. All data is measured after 24 hours. The test was done at 20° C.

Moisture Vapour Transmission Rate

Moisture vapour transmission rate (MVTR) is measured in grams per square meter (g/m$^2$) over a 24 hours period using an inverted cup method.

A container or cup that was water and water vapour impermeable having an opening of Ø35 mm was used. 20 mL saline water (0.9% NaCl in demineralised water) was placed in the container and the opening was sealed with the test adhesive mounted on a highly permeable polyurethane (PU) backing film (BL9601 foil from Intellicoat). The container was placed in an electrically heated cabinet and the container or cup was placed upside down, such that the water was in contact with the adhesive. The cabinet was maintained at 32° C. The film reference is used in all experiments to control for any variations in testing conditions.

The weight loss of the container was followed as a function of time. The weight loss was due to water transmitted through the adhesive and/or film. This difference was used to calculate the MVTR of the test adhesive film. MVTR was calculated as the weight loss per time divided by the area of the opening in the cup (g/m$^2$/24 h).

The MVTR of a material is a linear function of the thickness of the material. Thus, when reporting MVTR to characterize a material, it is important to inform the thickness of the material which MVTR was reported.

Finally, we noted that by using this method, we introduced an error by using a supporting PU film. Utilizing the fact that the adhesive/film laminate was a system of two resistances in series eliminated the error. When the film and the adhesive are homogeneous, the transmission rate may be expressed as:

$$1/P(\text{measured}) = 1/P(\text{film}) + 1/P(\text{adhesive}).$$

Hence, by knowing the film permeability and thickness of the adhesive, it is possible to calculate the true permeability of the adhesive, P(adhesive), using the following expression:

$$P(\text{adhesive}) = d(\text{adhesive})/150 \, \mu m * 1/(1/P(\text{measured}) - 1/P(\text{film})),$$

where d(adhesive) was the actual measured thickness of the adhesive and P(film) was the MVTR of the film without any adhesive on and P(measured) was the actual measured MVTR.

EXAMPLES

BioPSA 7-4600, 7-4560 and 7-4400 are used as components herein. These polymers were obtained from Dow Corning and were made by reacting a poly(dimethyl siloxane) terminated with two terminal OH groups with a resin. By changing the resin to polymer ratio, it is possible to tune the properties (Table A)

TABLE A

Different parent sticky polymers and properties used in examples

| Sticky polymer | Resin/Polymer | Property |
|---|---|---|
| BioPSA 7-4600 | 55/45 | High tack |
| BioPSA 7-4500 | 60/40 | Medium tack |
| BioPSA 7-4400 | 65/35 | Low tack |

TABLE B

Different BioPSA derived materials used in examples to give adhesion

| Sticky polymer (wt %) | Poly(dimethyl siloxane) oil (wt %) |
|---|---|
| 7-4560 | 100 cSt (10%) |
| 7-4560 (90%) | 300,000 cSt (10%) |
| 7-4560 (90%) | 1,000 cSt (10%) |
| 7-4600 (90%) | 100 cSt (10%) |
| 7-4400 (80%) | 100 cSt (20%) |
| 7-4560 (90%) | 12,500 cSt (10%) |
| 7-4560 (45%) + 7-4400 (40%) | 300,000 cST (5%) + 100 cST (10) |

The commercially available Trio Silken Stoma Gel was used in some examples. Compositions like the Trio Silken Stoma Gel typically comprise an OH-terminated PDMS as the reactive polymer, methyl trimethoxy silane as crosslinker, a titanium catalyst, and silica particles. Approximate amounts are given in the table below.

TABLE C

Main components of a gel with properties like the Trio Silken Stoma Gel

| Component | Approximate contens | Comments |
|---|---|---|
| OH terminated PDMS (reactive polymer) | 84 wt % | Mn: 28,200 g/mol, Mw: 59,600 g/mol, PDI: 2.11 |
| Methyl trimethoxy silane | 0.85 wt % | |
| Titanium content | 1,000 ppm | |
| Silica particles | 10 wt % | |
| Other components | To reach 100% | |

Example Compositions

Composition 1 (BTHCS5): BioPSA 7-4560, Trio, and Mixed Hydrocolloids. 54:36:10 wt %

Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane Biatin film (30 µm) using an applicator. For the switch experiments, this composition was switched either in an oven at 32° C., or in a humidity cupboard (Binder KBF) at 32° C. and 50% relative humidity.

Composition 2 (BTHCS9): BioPSA 7-4560, Trio, and Potato Starch. 54:36:10 wt %

Trio Silken (18 g, 36 wt %, Trio Healthcare) was mixed with a mixture of potato starch (5 g, 10 wt %) using Speedmixer at 3000 rpm for 3 minutes. An unreactive silicone polymer, BioPSA (27 g, 54 wt %, Dow Corning 7-4560), was added to the mixture, and the mixture was mixed using Speedmixer for additional 3 minutes at 3000 rpm. The resulting mixture was coated on a PU Biatin film using an applicator. For the switch experiments, this composition was switched in an oven at 32° C.

Composition 3 (BTHCS8): BioPSA 7-4560, Trio, and CMC. 54:36:10 wt %

Trio Silken (18 g, 36 wt %, Trio Healthcare) was mixed with a mixture of carboxymethylcellulose (5 g, 10 wt %) using Speedmixer at 3000 rpm for 3 minutes. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a PU Biatin film (30 µm) using an applicator. For the switch experiments, this composition was switched in an oven at 32° C.

Composition 4 (BTHCS5-32): BioPSA 7-4560, Trio, and Dried (80° C.) Mixed Hydrocolloids. 54:36:10 wt %

Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). Hydrocolloids were dried prior to use in an oven at 80° C. The total moisture content of the hydrocolloids were measured as 2.28 wt %. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane Biatin film (30 µm) using an applicator. For the switch experiments, this composition was switched in an oven at 32° C.

Composition 5 (BTHCS8-25): BioPSA 7-4560, Trio, and Dried (80° C.) CMC. 54:36:10 Wt %

Trio Silken (18 g, 36 wt %, Trio Healthcare) was mixed with dried CMC (5 g, 10 wt using Speedmixer at 3000 rpm for 3 minutes. Hydrocolloids were dried prior to use in an oven at 80° C. The total moisture content of the hydrocolloids were measured as 2.73 wt %. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a PU Biatin film (30 µm) using an applicator. For the switch experiments, this composition was switched in an oven at 32° C.

Composition 6 (BTHCS17): BioPSA 7-4560, Trio, and Dried (80° C.) Mixed Hydrocolloids. 24:36:40 wt %

Trio Silken (12 g, 24 wt %, Trio Healthcare) was mixed with a mixture of hydrocolloids (20 g, 40 wt %) using Speedmixer at 3000 rpm for 3 minutes. The hydrocolloid mixture consists of carboxymethyl cellulose (20 wt Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt LM 12 CG-Z/200, CP Kelco). The hydrocolloids were dried at 80° C. before being added to the formulation until they reached a water content of 2.43 wt %. An unreactive silicone polymer, BioPSA (18 g, 36 wt %, Dow Corning 7-4560) was added to the mixture, and the mixture was mixed using Speedmixer for additional 3 minutes at 3000 rpm. The resulting mixture was coated on a film using an applicator, and the film was cured in an oven at 32° C. with a relative humidity of 50% before testing.

Composition 7 (BTHCS10): BioPSA 7-4560, Trio, and Dried (80° C.) Mixed Hydrocolloids. 45:30:25 wt %

Trio Silken (15 g, 30 wt %, Trio Healthcare) was mixed with a mixture of hydrocolloids (12.5 g, 25 wt %) using Speedmixer at 3000 rpm for 3 minutes. The hydrocolloid mixture consists of carboxymethyl cellulose (20 wt Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt LM 12 CG-Z/200, CP Kelco). The hydrocolloids were dried at 80° C. before being added to the formulation until they reached a water content of 2.16 wt %. An unreactive silicone polymer, BioPSA (22.5 g, 45 wt %, Dow Corning 7-4560) was added to the mixture, and the mixture was mixed using Speedmixer for additional 3 minutes at 3000 rpm. The resulting mixture was coated on a film using an applicator, and the film was cured in an oven at 32° C. with a relative humidity of 50% before testing.

Composition 8 (B4400TAS): BioPSA 7-4400 with 100 cSt PDMS, Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4400+ 100 cSt PDMS oil (80:20) wt %) was added and mixed at 3000 rpm for additional 3 minutes. The resulting mixture was coated on a film using an applicator, and the film was cured in an oven at 32° C. with a relative humidity of 50% before testing.

Composition 9 (B4600TAS): BioPSA 7-4600 with 100 cSt PDMS Oil, Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4600+ 100 cSt PDMS oil (90:10) wt %) was added and mixed at 3000 rpm for additional 3 minutes. The resulting mixture was coated on a film using an applicator, and the film was cured in an oven at 32° C. with a relative humidity of 50% before testing.

Composition 10 (DBTAS1): BioPSA 7-4560 with 300, 000 cSt PDMS Oil, Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4560+ 300 000 cSt PDMS oil (90:10) wt %) was added and mixed at 3000 rpm for additional 3 minutes. The resulting mixture was coated on a film using an applicator, and the film was cured in an oven at 32° C. with a relative humidity of 50% before testing.

Composition 11 (DBTAS5): BioPSA 7-4560 with 12,500 cSt PDMS Oil, Trio, and Dried (140° C.) CMC. 36:24:40 wt %:

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4560+ 12500 cSt PDMS oil (90:10) wt %) was added and mixed at 3000 rpm for additional 3 minutes. The resulting mixture was coated on a film using an applicator, and the film was cured in an oven at 32° C. with a relative humidity of 50% before testing.

Composition 12 (DBTAS2): BioPSA 7-4560 with 1,000 cSt PDMS Oil, Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4560+ 1000 cSt PDMS oil (90:10) wt %) was added and mixed at 3000 rpm for additional 3 minutes. The resulting mixture was coated on a film using an applicator, and the film was cured in an oven at 32° C. with a relative humidity of 50% before testing.

Composition 13 (TABS): BioPSA 7-4560, Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4560) was added and mixed at 3000 rpm for additional 3 minutes. The resulting mixture was coated on a film using an applicator, and the film was cured in an oven at 32° C. with a relative humidity of 50% before testing.

Composition 14 (DBTAS6): BioPSA 7-4560 and 7-4400 with 300,000 cST PDMS Oil and 100 cST PDMS Oil (45:40:5:10), Trio, and Dried (140° C.) CMC. 36:24:40 wt %

Trio Silken Stoma Gel (12 g, Trio Healthcare), a commercial stoma gel, and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (18 g, Dow Corning 7-4560+ 7-4400+300 000 cST PDMS oil and 100 cST PDMS oil (45:40:5:10) wt %) was added and mixed at 3000 rpm for additional 3 minutes. The resulting mixture was coated on a film using an applicator, and the film was cured in an oven at 32° C. with a relative humidity of 50% before testing.

Composition 15 (3g_R812BA3): Sealant No. 1, BioPSA 7-4560, and Dried (140° C.) CMC. 10:50:40 wt %

A silanol terminated poly(dimethyl siloxane) (19.76 g, DMS-S31 (1000 cST, Gelest)) was mixed with methoxytrimethyl silane (1.2 g, Sigma Aldrich) at 1000 rpm for 30 s using Speedmixer™. Hydrophobic silica particles (3.7 g, Aerosil R812, Evonik) was added and mixed for at 3000 rpm for 1 minute. Finally, the resulting material was mixed with a titanium 2-ethylhexoxide (0.2 g, AKT 867, Gelest) at 3000 rpm for 1 minute to obtain the sealant.

Sealant composition no. 1=DMS S31: Methoxytrimethyl silane: Catalyst (AKT 867): Silica particles (R812) (79:5.04: 0.83:15.1) wt %

Sealant composition no. 1 (5 g), and vacuum dried Akucell (20 g, Akucell AF 2881, Akzo Nobel) were mixed using Speedmixer™ at 3000 rpm for additional 3 minutes. A silicone polymer, BioPSA (25 g, Dow Corning 7-4560) was added and mixed at 3000 rpm for additional 3 minutes. The resulting mixture was coated on a film using an applicator or using a press for 30 s, and the film was cured in an oven at 32° C. with a relative humidity of 50% before testing.

Composition 16 (5c_R812BA2): Sealant No. 2, BioPSA 7-4560, and Dried (140° C.) CMC. 10:50:40 wt %

A silanol terminated poly(dimethyl siloxane) (20.39 g, DMS-S35 (5000 cST, Gelest) was mixed with methoxytrimethyl silane (0.59 g, Sigma Aldrich) at 1000 rpm for 30 s using Speedmixer™. Hydrophobic silica particles (3.7 g, Aerosil R812, Evonik) was added and mixed for at 3000 rpm for 1 minute. Finally, the resulting material was mixed with a titanium 2-ethylhexoxide (0.22 g, AKT 867, Gelest) at 3000 rpm for 1 minute to obtain the sealant.

Sealant composition no. 2=DMS S35:Methoxytrimethyl silane:Catalyst (AKT 867):Silica particles (R812) (81.82: 2.37:0.91:14.88) wt %

Sealant composition no. 2 (5 g), and vacuum dried Akucell (20 g, Akucell AF 2881, Akzo Nobel) using Speedmixer™ at 3000 rpm for 3 minutes. (Akucell AF 2881 was dried under vacuum at 140° C. until reaching a water content of less than 1 wt %.). A silicone polymer, BioPSA (25 g, Dow Corning 7-4560 was added and mixed at 3000 rpm for additional 3 minutes. The resulting mixture was coated on a film using an applicator, and the film was cured in an oven at 32° C. with a relative humidity of 50% before testing.

Comparative: Trio Only and Bio PSA Only

Composition 17 (Sample Code BTHCS105): BIOPSA (85 wt %)+Hydrocolloids (15 Wt %) (Wt % Ratio BioPSA/ Hhydrcolloids: 6.07)

An unreactive silicon polymer, BioPSA (42 g, 85 wt %, Dow Corning 7-4560) was mixed with a mixture of hydrocolloids using Speedmixer™ at 3000 rpm for 3 minutes. The hydrocolloid mixture consists of carboxymethyl cellulose (20 wt %, Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt %, pectin LM 12 CG-Z/200, CP Kelco). The resulting mixture was pressed and used for further testing. Note: We tried to coat this mixture using an applicator as for the rest of the formulations, but this was not possible. Therefore, we pressed it.

Composition 18 (Pure Trio-Humidity Cupboard):

Trio Silken (18 g, 36 wt %, Trio Healthcare) was directly coated on a film, and cured in a humidity cupboard at 32° C. and 50 relative humidity.

In Table D are shown, for comparison only, the peel results on compositions 17 and 18. "AB" and "CB" denote the failure mode of the adhesive in the peel test. AB is adhesive break and CB is cohesive break. Cohesive break means that the adhesive cannot be pulled off the substrate in one piece but rather comes apart cohesively and leaves residue on the substrate. Cohesive break generally results from the cohesive forces holding the adhesive together being weaker than the adhesive forces holding the adhesive and the substrate together. Adhesive break means that the adhesive comes off the substrate in one piece without breaking apart or leaving substantial residue.

The results clearly demonstrate that the Trio Silken Stoma Gel on its own does not result in a properly adhesive composition, in that the peel forces of the cured gel are extremely low.

TABLE D

| Comparative peel results | | | | | |
|---|---|---|---|---|---|
| Composition | Failure type | $1^{st}$ peel force (N) type | $2^{nd}$ peel force (N) | Thickness (μm) | Cure time |
| 17 | AB | 26 ± 0.83 | 32 ± 11 | 1,100 ± 566 | n/a |
| 18 | CB | 0.33 ± 0.12 | n/a | 464 | 0 |

TABLE D-continued

Comparative peel results

| Composition | Failure type | 1st peel force (N) | 2nd peel force (N) | Thickness (μm) | Cure time |
|---|---|---|---|---|---|
| 18 | AB | 0.06 ± 0.005 | 0.053 ± 0.025 | 399 ± 15 | 1 h |
| 18 | AB | 0.1 ± 0.023 | 0.09 ± 0.027 | 400 | 6 h |

In Table E are shown the results for the comparative measurements of the viscosity of the Trio Silken Stoma Gel.

TABLE E

Comparative viscosity results

| Composition | Curing time | Complex Viscosity (Pa · s) |
|---|---|---|
| 18 | 0 h | 1,600 |
| 18 | 3.5 h | 21,500 |

TABLE F

Water absorption of Trio Silken Stoma Gel

| Composition | Adhesive thickness (μm) | Water absorption (g/cm$^2$) | Time | Curing time in oven before water absorption test |
|---|---|---|---|---|
| 18 | 400 | 0.0011 | 5 min | 0 |
| 18 | 400 | 0.0042 | 30 min | 0 |
| 18 | 400 | 0.0044 | 2 h | 0 |
| 18 | 400 | 0.0016 | 24 h | 0 |

The data in Table F show that Trio Silken stoma gel does not absorb water.

Results

TABLE 1a

| Comp. # | 1a[4] | 1b[5] | 2 | 3 | 4 | 5 |
|---|---|---|---|---|---|---|
| Reactive component | Trio | Trio | Trio | Trio | Trio | Trio |
| BioPSA Adhesive | 7-4560 | 7-4560 | 7-4560 | 7-4560 | 7-4560 | 7-4560 |
| Hydrocolloids | 10% mix | 10% mix | 10% potato starch | 10% CMC | 10% dry mix | 10% dry CMC |
| First peel[1] N/25 mm | 3.04 | 2.24 | 3.39 | 2.44 | 1.14 | 1.03 |
| Repeated peel[2] N/25 mm | 3.02 | 3.70 | 3.10 | 2.04 | 1.26 | 1.01 |
| Viscosity[3] Pa s, 0.01 Hz | 351 | 351 | 310 | 328 | 1,072 | 1,557 |

[1]Measured after switch on substrate.
[2]Measured after switch on substrate, detachment, and re-attachment.
[3]Complex viscosity measured before switch.
[4]Oven-cured sample.
[5]Humidity cupboard-cured sample TABLE 1b

| Comp. # | 6 | 7 | 8 | 9 | 10 | 11 |
|---|---|---|---|---|---|---|
| Reactive component | Trio | Trio | Trio | Trio | Trio | Trio |
| BioPSA Adhesive | 7-4560 | 7-4560 | 7-4400 + 100 cSt | 7-4600 + 100 cSt | 7-4560 + 300k cSt | 7-4560 + 12.5k cSt |
| Hydrocolloids | 40% dry (80° C.) mix | 20% dry mix | 40% dry CMC | 40% dry CMC | 40% dry CMC | 40% dry CMC |
| First peel[1] N/25 mm | 1.47 | 1.86 | 1.98 | 3.21 | 2.22 | 1.93 |
| Repeated peel[2] | 1.16 | 1.52 | 1.99 | 1.84 | 1.87 | 1.58 |
| Viscosity[3] Pa s, 0.01 Hz | 2,366 | 795 | 572 | 4,094 | 987 | 505 |

[1]Measured after switch on substrate.
[2]Measured after switch on substrate, detachment, and re-attachment.
[3]Complex viscosity measured before switch.

TABLE 1c

| Comp. # | 12 | 13 | 14 | 15 | 16 |
|---|---|---|---|---|---|
| Reactive component | Trio | Trio | Trio | Sealant no. 1 | Sealant no. 2 |
| BioPSA-based adhesive | 7-4560 + 1 k cSt | 7-4560 | 7-4560 + 7-4400 + 4.4 k and 300 k cSt | 7-4560 | 7-4560 |
| Hydrocolloids | 40% dry CMC | 40% dry (140° C.) CMC | 40% dry CMC | 40% dry CMC | 40% dry CMC |
| First peel[1] N/25 mm | 1.95 | 2.18 | 1.78 | 3.13 | 4.95 |
| Repeated peel[2] | 1.39 | 2.18 | 1.52 | 3.03 | 4.65 |
| Viscosity[3] Pa s, 0.01 Hz | 643 | 831 | 958 | 16,190 | 13,610 |

[1]Measured after switch on substrate.
[2]Measured after switch on substrate, detachment, and re-attachment.
[3]Complex viscosity measured before switch.

TABLE 2

Time dependency of complex viscosity

| Composition | Curing time | Complex viscosity at 0.01 Hz (Pa s) | Storage modulus (Pa) | Loss modulus (Pa) |
|---|---|---|---|---|
| 1a (oven cured) | 2 h | 554 | | |
| 1a (oven cured) | 24.3 h | 11,700 | | |
| 1a (oven cured) | 2 days | 32,200 | | |
| 1a (oven cured) | 7 days | 44,000 | | |
| 1b (humidity cupboard cured) | 24 h | 30,900 | | |
| 1b (humidity cupboard cured) | 50 h | 87,100 | | |
| 1b (humidity cupboard cured) | 7 days | 101,000 | | |
| 2 | 30 min | 363 | | |
| 2 | 2.5 h | 767 | | |
| 2 | 22 h | 15,000 | | |
| 2 | 47 h | 26,700 | | |
| 2 | 3 days | 31,500 | | |
| 3 | 2 h | 332 | | |
| 3 | 24 h | 7,590 | | |
| 3 | 43 h | 20,700 | | |
| 3 | 3 days | 25,900 | | |
| 4 | 30 min | 11,900 | 562 | 492 |
| 4 | 2 h | 47,500 | 2,840 | 941 |
| 4 | 24 h | 165,000 | 10,200 | 1,790 |
| 5 | 30 min | 20,200 | 1,160 | 514 |
| 5 | 2 h | 60,100 | 3,690 | 786 |
| 5 | 48 h | 95,500 | 5,910 | 1,050 |
| 5 | 71 h | 117,000 | 7,270 | 1,200 |
| 6 | 30 min | 70,500 | 3,820 | 2,240 |
| 6 | 25 h | 309,000 | 18,300 | 6,510 |
| 6 | 49 h | 390,000 | 23,300 | 7,740 |
| 7 | 30 min | 2,340 | 27 | 145 |
| 7 | 24.5 h | 117,000 | 7,140 | 1,690 |
| 8 | 24 h | 259,000 | 15,400 | 5,420 |
| 8 | 48 h | 269,000 | 16,000 | 5,560 |
| 9 | 4 h | 33,900 | 1,470 | 1,540 |
| 9 | 24 h | 312,000 | 18,700 | 7,450 |
| 10 | 24 h | 276,000 | 16,500 | 5,440 |
| 10 | 48 h | 340,000 | 20,300 | 6,730 |
| 11 | 4 h 20 min | 18,400 | 830 | 806 |
| 11 | 48 h | 288,000 | 17,300 | 5,490 |
| 12 | 23 h | 232,000 | 14,000 | 4,140 |
| 13 | 22 h | 270,000 | 15,900 | 5,770 |
| 14 | 26 h | 258,000 | 15,400 | 5,110 |
| 15 | 2 h | 61,100 | 2,520 | 2,890 |
| 15 | 4 h | 114,000 | 5,830 | 4,170 |
| 15 | 25 h | 249,000 | 13,300 | 8,270 |
| 16 | 2 h | 38,000 | 1,020 | 2,160 |
| 16 | 4 h | 50,000 | 1,830 | 2,560 |
| 16 | 25.4 h | 148,000 | 7,430 | 5,540 |

TABLE 3

MVTR results on moisture curing examples after 48 h curing

| Sample | Adhesive thickness (μm) | MVTR 150 μm Adhesive + Film (g/m²/24 h) | MVTR 150 μm Adhesive (g/m²/24 h) |
|---|---|---|---|
| Composition 1a (Sample code BTHCS5-oven): | 336 | 439 | 477 |
| Composition 1b (Sample code BTHCS5-humidty cupboard): | 343 | 500 | 549 |
| Composition 2 (Sample code BTHCS9-oven | 382 | 499 | 548 |
| Foil used in Composition 1-2 | 30 | Not applicable | Not applicable |
| Composition 3 (Sample code BTHCS8-oven | 531 | 572 | 641 |
| Foil used in Composition 3 | 30 | Not applicable | Not applicable |

TABLE 4

Erosion results on moisture curing examples after 48 h curing

| Sample | Adhesive thickness (μm) | Eroded away | Swelling |
|---|---|---|---|
| Composition 1a (BTHCS5-oven) | 336 ± 19 | No | 0 |
| Composition 1b (BTHCS5-humidty cupboard) | 376 ± 16 | No | 0 |
| Composition 2 (BTHCS9) | 356 ± 1 | No | 0 |
| Composition 3 (BTHCS8) | 440 ± 46 | No | 0 |

TABLE 5

Water absorption results on moisture curing examples after 48 h curing

| Sample | Adhesive thickness (μm) | Water absorption (g/cm²/2 h) |
|---|---|---|
| Composition 1a (BTHCS5-oven) | 365 ± 21 | 0.01 |
| Composition 1b (BTHCS5-humidty cupboard) | 475 ± 35 | 0.01 |
| Composition 2 (BTHCS9) | 440 | 0.01 |
| Composition 3 (BTHCS8) | 450 | 0.01 |
| Composition 6 | 400 | 0.03 |
| Composition 7 | 400 | 0.01 |
| Composition 8 | 400 | 0.03 |
| Composition 9 | 400 | 0.02 |
| Composition 10 | 400 | 0.02 |
| Composition 11 | 400 | 0.02 |

TABLE 5-continued

Water absorption results on moisture curing examples after 48 h curing

| Sample | Adhesive thickness (μm) | Water absorption (g/cm²/2 h) |
|---|---|---|
| Composition 12 | 400 | 0.02 |
| Composition 14 | 400 | 0.02 |

The invention claimed is:

1. A moisture-curable adhesive composition comprising:
   a reactive component, wherein the reactive component comprises a reactive silicone polymer or a mixture of reactive silicone polymers;
   an adhesive component, wherein the adhesive component comprises a cured polycondensed organopolysiloxane resin that is a reaction product or products of a silanol terminated organopolysiloxane and a silicate organopolysiloxane resin containing at least one $RSiO_{3/2}$ or $SiO_{4/2}$ siloxyl unit, wherein each R, individually, is H, an alkyl group, aryl group, a reactive functional group or an alkoxy group;
   a cross-linker;
   a catalyst; and
   a hydrocolloid, wherein the hydrocolloid is selected from guar gum, locust bean gum, pectin, potato starch, alginates, gelatine, xanthan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

2. The moisture-curable adhesive composition according to claim 1, wherein the reactive silicone polymer or mixture of reactive silicone polymers comprises a polysiloxane of the formula (I):

$$X-R_1R_2Si-(O-SiR_1R_2)_n-Y \quad (I)$$

wherein X and Y are OH;
   wherein $R_1$ and $R_2$ independently are the same or different and selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group; and
   wherein n is a number from 1 to 10,000.

3. The moisture-curable adhesive composition according to claim 1, wherein the reactive silicone polymer or mixture of reactive silicone polymers comprises a polysiloxane of the formula (II):

$$(R_3O)_m-Si(R_4)_{3-m}-(O-SiR_1R_2)_n-Si(R_4)_{3-k}-(OR_3)_k \quad (II)$$

wherein k and m independently are integers from 0 to 3, provided that k+m>0;
   wherein $R_1$, $R_2$, and $R_4$ independently are the same or different and selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group;
   wherein $R_3$ is $C_1$-$C_{10}$ alkyl; and
   wherein n is a number from 1 to 10,000.

4. The moisture-curable adhesive composition according to claim 1, wherein the reactive silicone polymer or mixture of reactive silicone polymers comprises a polysiloxane of the formula (III):

$$W-Z-W \quad (III)$$

wherein W is selected from the group consisting of —Si(R1)2OH and —Si(R")2-(D)d-R'"—SiR"k(OR5)3-k, wherein $R_1$ is selected from the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group; wherein D is —R'"—(Si(R")2-O)r-Si(R")2- and R" is selected from the group consisting of a $C_1$-$C_6$ alkyl, a vinyl group, a phenyl group, and a fluorinated $C_1$-$C_6$ alkyl, R'" is a divalent hydrocarbon group, r is an integer between 1 and 6, and d is 0 or an integer from 1 to 100, R5 is a $C_1$-$C_6$ alkyl or alkoxy group, and k has is 0, 1 or 2;
   wherein Z is a linear polysiloxane polymer backbone.

5. The moisture-curable adhesive composition according to claim 4, wherein Z is a polysiloxane of the formula (IV):

$$-[SiO_{(4-p)/2}(R_1)_p]_b- \quad (IV)$$

wherein b is an integer from 50 to 5,000, p is on average 1.9-2.0, and $R_1$ is selected form the group consisting of $C_1$-$C_{10}$ alkyl, $C_1$-$C_{10}$ alkyl substituted at one or more carbons with one or more halogen atoms, $C_1$-$C_{18}$ alkyl substituted at one or more carbons with a cyano (—CN) group, phenyl, and phenyl substituted at one or more carbons with a halogen atom or a cyano group.

6. The moisture-curable adhesive composition according to claim 1, wherein the silanol terminated organopolysiloxane comprises a structure:

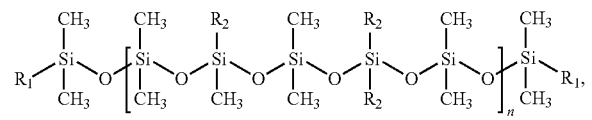

wherein $R_1$ is OH;
   $R_2$ is methyl, phenyl, or vinyl; and
   n is from 1 to 500.

7. The moisture-curable adhesive composition according to claim 1, wherein the cross-linker contains at least two hydrolysable groups and is selected from the group consisting of a silicone, an organic polymer, a monosilane molecule, and a disilane molecule.

8. The moisture-curable adhesive composition according to claim 1, wherein the cross-linker is a monosilane of the formula (V):

$$R^{IV}_{4-q}Si(OR_5)_q \quad (V)$$

wherein $R^{IV}$ is an organic radical selected from the group consisting of linear alkyl, branched alkyl, allyl, phenyl, substituted phenyl, acethoxy, and oxime;
   wherein $R_5$ is selected from the group consisting of hydrogen, methyl, and ethyl; and
   wherein q is 0 or an integer from 1 to 4, or
   wherein the cross-linker is a disilane of the formula (VI):

$$Si(OR_7)_tR^VSi(OR_7)_q \quad (VI)$$

wherein t and q independently are integers from 1 to 3;
   wherein $R^V$ is an organic or poly-siloxane-based moiety; and
   wherein $R_7$ is selected from the group consisting of hydrogen, methyl, and ethyl.

9. The moisture-curable adhesive composition according to claim 1, wherein the cross-linker is selected from the group consisting of methyltri(methoxy)silane (MTM), vinyltrimethoxysilane, methyltriethoxysilane, vinyltriethoxysilane, isobutyltrimethoxysilane (iBTM), ethyltrimethoxysilane, vinyltriethoxysilane, phenyltrimethoxysilane, oximosilanes, acetoxy silane, acetonoxime silane, and enoxy silane.

10. The moisture-curable adhesive composition according to claim 1, wherein the catalyst is a metal-containing catalyst comprising a metal selected from the group consisting of tin, lead, antimony, iron, cadmium, barium, manganese, zinc, chromium, cobalt, nickel, aluminium, gallium, germanium, titanium and zirconium.

11. The moisture-curable adhesive composition according to claim 10, wherein the catalyst is a titanium catalyst.

12. The moisture-curable adhesive composition according to claim 1, wherein the hydrocolloid is present in an amount from 30 weight percent to 50 weight percent.

13. The moisture-curable adhesive composition according to claim 1, further comprising an adhesion promoter.

14. The moisture-curable adhesive composition according to claim 13, wherein the adhesion promoter is 3-aminopropyltrimethoxysilane, 3-aminopropyltriethoxysilane, 3-glycidoxypropyltrimethoxysilane, 2-3(3,4-epoxycyclohexyl)ethyltrimethoxysilane, 3-mercaptopropyltrimethoxysilane, or methacryloxypropyltrimethoxysilane.

15. The moisture-curable adhesive composition according to claim 1, wherein the adhesive composition is a one-part curable composition.

16. A method to prepare a moisture-curable adhesive composition according to claim 1, comprising the step:
providing one or more reactive silicone polymers;
combining the one or more reactive silicone polymer(s) with a cured polycondensed organopolysiloxane resin that is a reaction product or products of a silanol terminated organopolysiloxane and a silicate organopolysiloxane resin containing at least one $RSiO_{3/2}$ or $SiO_{4/2}$ siloxyl unit, wherein each R, individually, is H, an alkyl group, aryl group, a reactive functional group or an alkoxy group, a cross-linker; a source of moisture; and a catalyst to form the moisture-curable adhesive composition.

17. A method to releasably and adhesively attach a medical device to a skin surface comprising the steps:
providing a medical device comprising a moisture-curable adhesive composition without water, the moisture-curable adhesive composition comprising a reactive component, wherein the reactive component comprises a reactive silicone polymer or a mixture of reactive silicone polymers; an adhesive component, wherein the adhesive component comprises a cured polycondensed organopolysiloxane resin that is a reaction product or products of a silanol terminated organopolysiloxane and a silicate oranopolysiloxane resin containing at least one $RSiO_{3/2}$ or $SiO_{4/2}$ siloxyl unit, wherein each R, individually, is H, an alkyl group, aryl group, a reactive functional group or an alkoxy group; a cross-linker; and a catalyst;
applying the moisture-curable adhesive to the skin surface;
exposing the moisture-curable adhesive to moisture, thereby switching the moisture-curable adhesive from a liquid state to an adhesive state.

18. A packaged product comprising:
a moisture-curable adhesive composition comprising a reactive component, wherein the reactive component comprises a reactive silicone polymer or a mixture of reactive silicone polymers;
an adhesive component, wherein the adhesive component comprises a cured polycondensed organopolysiloxane and a silicate oranopolysiloxane resin containing at least one $RSiO_{3/2}$ or $SiO_{4/2}$ siloxyl unit, wherein each R, individually, is H, an alkyl group, aryl group, a reactive functional group or an alkoxy group;
a cross-linker;
and a catalyst; and
instructions to apply the moisture-curable composition to a skin surface in the presence of moisture.

19. The packaged product according to claim 18, wherein the packaged product further comprises a medical device associated with the packaged product, wherein the medical device is an ostomy device.

* * * * *

UNITED STATES PATENT AND TRADEMARK OFFICE
CERTIFICATE OF CORRECTION

PATENT NO. : 10,729,806 B2
APPLICATION NO. : 15/569777
DATED : August 4, 2020
INVENTOR(S) : Bingol et al.

It is certified that error appears in the above-identified patent and that said Letters Patent is hereby corrected as shown below:

In the Specification

In Column 7, Line 2, delete "(would" and insert -- (wound --, therefor.

In Column 7, Line 14, delete "form" and insert -- from --, therefor.

In Column 7, Line 36, delete "form" and insert -- from --, therefor.

In Column 8, Line 13, delete "DMS-535," and insert -- DMS-S35, --, therefor.

In Column 8, Line 16, delete "($M_e$)" and insert -- ($M_n$) --, therefor.

In Column 9, Line 21, delete "($R^2_2SiO_{2/2}$)$_b$," and insert -- (ii) ($R^2_2SiO_{2/2}$)$_b$ --, therefor.

In Column 18, Line 11, delete "form" and insert -- from --, therefor.

In Column 18, Line 27, delete "form" and insert -- from --, therefor.

In Column 18, Line 56, delete "form" and insert -- from --, therefor.

In Column 18, Line 63, delete "form" and insert -- from --, therefor.

In Column 25, Line 38, delete "10 wt" and insert -- 10 wt%) --, therefor.

In Column 25, Line 53, delete "(20 wt" and insert -- (20 wt%, --, therefor.

In Column 25, Line 56, delete "(10 wt" and insert -- (10 wt%, --, therefor.

In Column 26, Line 4, delete "(20 wt" and insert -- (20 wt%, --, therefor.

Signed and Sealed this
Second Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,729,806 B2

In Column 26, Line 7, delete "(10 wt" and insert -- (10 wt%, --, therefor.

In Column 27, Line 20, delete "(TABS):" and insert -- (TAB5): --, therefor.

In the Claims

In Column 33, Line 39, in Claim 2, delete "form" and insert -- from --, therefor.

In Column 33, Line 55, in Claim 3, delete "form" and insert -- from --, therefor.

In Column 34, Line 23, in Claim 5, delete "form" and insert -- from --, therefor.

In Column 36, Line 29, in Claim 18, delete "organopolysiloxane" and insert -- organopolysiloxane resin that is a reaction product or products of a silanol terminated organopolysiloxane --, therefor.